US007413860B2

(12) United States Patent
Nezu et al.

(10) Patent No.: US 7,413,860 B2
(45) Date of Patent: Aug. 19, 2008

(54) SYSTEMIC CARNITINE DEFICIENCY GENE AND USES THEREOF

(75) Inventors: Jun-Ichi Nezu, Ibaraki (JP); Asuka Ose, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 236 days.

(21) Appl. No.: 10/940,500

(22) Filed: Sep. 13, 2004

(65) Prior Publication Data

US 2005/0020531 A1 Jan. 27, 2005

Related U.S. Application Data

(60) Division of application No. 09/798,743, filed on Mar. 2, 2001, now Pat. No. 6,790,831, which is a continuation of application No. PCT/JP99/04853, filed on Sep. 7, 1999.

(30) Foreign Application Priority Data

Sep. 7, 1998 (JP) ................................. 10/252683

(51) Int. Cl.
*C07H 21/04* (2006.01)
*C12Q 1/68* (2006.01)
(52) U.S. Cl. ........................... 435/6; 435/7.1; 536/23.5; 530/350; 530/387
(58) Field of Classification Search .................. 514/12; 530/350, 387; 536/23.5; 435/6, 7.1
See application file for complete search history.

(56) References Cited

U.S. PATENT DOCUMENTS 6,063,623 A 5/2000 Koepsell et al.

FOREIGN PATENT DOCUMENTS

| EP | 0 699 753 | 3/1996 |
|---|---|---|
| JP | 8-81497 | 3/1996 |
| WO | WO 97/42321 | 11/1997 |
| WO | WO 99/13072 | 3/1999 |
| WO | WO 00/14210 | 3/2000 |

OTHER PUBLICATIONS

Lamhonwah et al., "Carnitine Uptake Defect: Frameshift Mutations in the Human Plasmalemmal Carnitine Transporter Gene," Biochem. Biophys. Res. Commun., 252:396-401, 1998.
Lu et al., "A Missense Mutation of Mouse OCTN2, a Sodium-Dependent Carnitine Cotransporter, in the Juvenile Visceral Steatosis Mouse," Biochem. Biophys. Res. Commun., 252:590-594, 1998.
Nezu et al., "Primary systemic carnitine deficiency is cuased by mutations in a gene encoding sodium ion-dependent carnitine transporter," Nature Genetics, 21:91-94, 1999.
Tamai et al., "Molecular and Functional Identification of Sodium Ion-dependent, High Affinity Human Carnitine Transporter OCTN2," J. Biol. Chem., 273:20378-20382, 1998.
Wang et al., "Mutations in the organic cation/carnitine transporter OCTN2 in primary carnitine deficiency," Proc. Natl. Acad. Sci. USA, 96:2356-2360, 1999.
Wu et al., "cDNA Sequence, Transport Function, and Genomic Organization of Human OCTN2, a New Member of the Organic Cation Transporter Family," Biochem. Biophys. Res. Commun., 246:589-598, 1998.
Shoji et al., "Evidence for Linkage of Human Primary Systemic Carnitine Deficiency with D5S436: a Novel Gene Locus on Chromosome 5q," Am.J.Hum.Genet. 63:101-108, 1998.
Okita et al., "Definition of the Locus Responsible for Systemic Carnitine Deficiency within a 1.6-cM Region of Mouse Chromosome 11 by Detailed Linkage Analysis," Genomics 33:289-91, 1996.
Tsuji, A, "Membrane Transport of Carnitine, a Major Factor on Fatty Acid Metabolism, and its Deficiency Syndromes," Saibo Kogaku (Cell Technology) 18:1698-1706, 1999 (English abstract attached).
Masuda M, et al., "A Novel Gene Suppressed in the Ventricle of Carnitine-deficient Juvenile Visceral Steatosis Mice," FEBS Lett, 408:221-4, 1997.
I. Tein et al., "Impaired Skin Fibroblast Carnitine Uptake in Primary Systemic Carnitine Deficiency Manifested by Childhood Carnitine-Responsibe Cardiomyopathy", Pediatric Research, vol. 28, No. 3, pp. 247-255 (1990).
Nezu et al. "A Step Forward in Elucidating the Mechanism of Fatty Acid Metabolism: Discovery of OCTN2 Gene Responsible for Systemic Carnitine Deficiency, and Significance Thereof," Medikaru Asahi (Asahi Monthly J. of Medicine) 28:26-29, 1999, and English translation thereof.
Barrett et al., "Structure and function of facilitative sugar transporters," *Curr. Opin. Cell Biol.*, 11:496-502 (1999).
Bisson et al., "Yeast Sugar Transporters," *Crit. Rev. Biochem. Molec. Biol.*, 28:259-308 (1993).
Bork, "Powers and Pitfalls in Sequence Analysis: The 70% Hurdle," *Genome Res.*, 10:398-400 (2000).
Bork et al., "Go hunting in sequence databases but watch out for the traps," *Trends Genet.*, 12:425-427 (1996).
Bowie et al., "Deciphering the Message in Protein Sequences: Tolerance to Amino Acid Substitutions," *Science*, 247:1306-1310 (1990).
Brenner, "Errors in genome function," *Trends Genet.*, 15:132-133 (1999).
Chun et al., "Expression of Human Polyspecific Renal Organic Cation Transport Activity in *Xenopus laevis* Oocytes," *J. Pharm. Sci.*, 86:753-755 (1997).
Doerks et al., "protein annotation: detective work for function prediction," *Trends Genet.*, 14:248-250 (1998).
Dubuisson et al., "Ontogenic expression of the $Na^+$-independent organic anion transporting polypeptide (oatp) in rat liver and kidney," *J. Hepatol.*, 25:932-940 (1996).
GenBank Accession No. AA024584, 2 pages (Aug. 14, 1996).
GenBank Accession No. AA189399, 2 pages (Jan. 20, 1997).

(Continued)

*Primary Examiner*—Chih-Min Kam
(74) *Attorney, Agent, or Firm*—Fish & Richardson P.C.

(57) ABSTRACT

The gene responsible for systemic carnitine deficiency was found to be the OCTN2 gene involved in the transportation of organic cations. This invention enables tests for this disease by detecting whether or not the OCTN2 gene has a mutation. Furthermore, systemic carnitine deficiency can be treated using the normal OCTN2 gene and its protein.

22 Claims, 9 Drawing Sheets

OTHER PUBLICATIONS

GenBank Accession No. AA428395, 2 pages (May 25, 1997).
GenBank Accession No. AB007448, 2 pages (Feb. 13, 1999).
GenBank Accession No. L81760, 2 pages (Apr. 9, 1997).
Gorboulev et al., "Cloning and Characterization of Two Human Polyspecific Organic Cation Transporters," *DNA Cell Biol.*, 16:871-881 (1997).
Gründemann et al., "Drug excretion mediated by a new prototype of polyspecific transporter," *Nature*, 372:549-552 (1994).
Gründemann et al., "Primary Structure and Functional Expression of the Apical Organic Cation Transporter from Kidney Epithelial LLC-PK$_1$ Cells," *J. Biol. Chem.*, 272:10408-10413 (1997).
Izquierdo et al., "Changing Patters of Transcriptional and Post-transcriptional Control of β-F$_1$-ATPase Gene Expression during Mitochondrial Biogenesis in Liver," *J. Biol. Chem.*, 270:10342-10350 (1995).
Koepsell et al., "Organic cation transporters," *Rev. Physiol. Biochem. Pharmacol.*, 150:36-90 (2003).
Koepsell et al., "The SLC22 drug transporter family," *Pflugers Arch.*, 447:666-676 (2004).
Liang et al., Trinucleotide Insertions, Deletions, and Point Mutations in Glucose Transporters Confer K$^+$Uptake in *Saccharomyces cerevisiae, Mol. Cell. Biol.*, 18:926-935 (1998).
Lopez-Nieto et al., "Molecular Cloning and Characterization of NKT, a Gene Product Related to the Organic Cation Transporter Family That Is Almost Exclusively Expressed in the Kidney," *J. Biol. Chem.*, 272:6471-6478 (1997).
Mikayama et al., "Molecular cloning and functional expression of a cDNA encoding glycosylation-inhibiting factor," *Proc. Natl. Acad. Sci. USA*, 90:10056-10060 (1993).
Ngo et al., "Computational Complexity, Protein Structure Prediction, and the Levinthal Paradox," *The Protein Folding Problem and Tertiary Structure Prediction*, pp. 492-495 (1994).
Okuda et al., "cDNA Cloning and Functional Expression of a Novel Rat Kidney Organic Cation Transporter, OCT2," *Biochem. Biophys. Res. Commun.*, 224:500-507 (1996).
Schömig et al., "Molecular cloning and characterization of two novel transport proteins from rat kidney," *FEBS Lett.*, 425:79-86 (1998).
Schweifer et al., "The *Lx1* gene maps to mouse Chromosome 17 and codes for a protein that is homologous to glucose and polyspecific transmembrane transporters," *Mamm. Genome*, 7:735-740 (1996).
Simonson et al., "Molecular cloning and characterization of a novel liver-specific transport protein," *J. Cell Sci.*, 107:1065-1072 (1994).
Skolnick et al., "From genes to protein structure and function: novel applications of computational approaches in the genomic era," *Trends Biotechnol.*, 18:34-39 (2000).
Smith et al., "The challenges of genome sequence annotation or "The devil is in the details"," *Nat. Biotechnol.*, 15:1222-1223 (1997).
Tamai et al., "Cloning and characterization of a novel human pH-dependent organic cation transporter," *FEBS Lett.*, 419:107-111 (1997).
Voet et al., *Biochemistry*, pp. 126-128 ("Chemical Evolution") and pp. 228-234 ("Abnormal Hemoglobins"), John Wiley and Sons Inc. (1990).
Wells, "Additivity of Mutational Effects in Proteins," *Biochemistry*, 29:8509-8517 (1990).
Yabuuchi et al., "Novel Membrane Transporter OCTN1 Mediates Multispecific, Bidirectional, and pH-Dependent Transport of Organic Cations," *J. Pharmacol. Exp. Ther.*, 289:768-773 (1999).
Zhang et al., "Cloning and Functional Expression of a Human Liver Organic Cation Transporter," *Mol. Pharmacol.*, 51:913-921 (1997).

Wild type

Ins C, nt226

SYSTEMIC CARNITINE DEFICIENCY GENE AND USES THEREOF

This application is a divisional of U.S. application Ser. No. 09/798,743, filed on Mar. 2, 2001, now U.S. Pat. 6,790,831, which is a continuation of PCT/JP99/04853, filed Sep. 7, 1999, and claims priority from Japanese Patent Application No. 10/252,683, filed Sep. 7, 1998.

TECHNICAL FIELD

This invention relates to molecules used in the testing and treatment of systemic carnitine deficiency, as well as methods for testing the disease.

BACKGROUND OF THE INVENTION

Systemic Carnitine Deficiency (SCD) is a human genetic disease inherited through autosomal recessive inheritance, the main symptoms being skeletal or cardiac muscle disorders (NIM 212140) (Roe, C. R. and Coates, P. M., Mitochondrial fatty acid oxidation disorder, The metabolic and molecular bases of inherited diseases 7th ed., edited by Scriver, C. R., Beaudet, A. L., Sly, W. S. and Valle, D., McGraw-Hill, New York, 1995, 1508-1509; Karpati, G. et al., The syndrome of systemic carnitine deficiency: clinical, morphologic, biochemical, and pathophysiologic features, Neurology 1975, 25:16-24). Serum carnitine levels and intra-tissue carnitine levels are known to be extremely low in these patients compared to healthy individuals. Carnitine is an indispensable co-factor in the long-chain fatty acid metabolism. A carnitine-mediated mechanism enables intracellular fatty acids to permeate mitochondrial outer and inner membranes, and energy is produced when these fatty acids undergo β-oxidation within the mitochondria (Walter, J. H., L-Carnitine, Arch Dis Child, 1996, 74:475-478; Bremer, J., Carnitine metabolism and functions, Physiol Rev, 1983, 1420-1480). The abnormal decrease of carnitine concentration in systemic carnitine deficiency patients is thought to be the direct cause of diseases in tissues such as muscles that require a large amount of energy. Membrane physiological studies done using fibroblasts from systemic carnitine deficiency patients have shown that these cells lack the mechanism to transport carnitine from the outside of the cell to the inside. A gene that encodes a protein involved in this mechanism is presumed to be the gene responsible for this disease (Tein, I. et al., Impaired skin fibroblast carnitine uptake in primary systemic carnitine deficiency manifested by childhood carnitine-responsive cardiomyopathy, Pediatr Res, 1990, 28:247-255). However, the gene responsible for systemic carnitine deficiency is yet to be isolated.

SUMMARY OF THE INVENTION

An objective of the present invention is to provide the gene responsible for systemic carnitine deficiency. Moreover, this invention aims to provide a molecule used in the testing and treatment of systemic carnitine deficiency, as well as a method for testing the disease.

The Inventors isolated several genes encoding proteins involved in the transport of organic cations. Among these, the Inventors discovered the human gene (human OCTN2 gene) having an activity to transport carnitine in a sodium ion dependent manner, and the corresponding mouse gene (mouse OCTN2 gene) (Japanese Patent Application Hei 9-260972, Japanese Patent Application Hei 10-156660). The Inventors thought that the isolated OCTN2 gene might be the gene responsible for systemic carnitine deficiency, and evaluated this possibility.

Specifically, the nucleotide sequence of the OCTN2 gene of the systemic carnitine deficiency mouse model and systemic carnitine deficiency patients were analyzed. As a result, the Inventors discovered the presence of various mutations in the OCTN2 gene of both the mouse model and systemic carnitine deficiency patients. In other words, for the first time in the world, the Inventors succeeded in revealing that systemic carnitine deficiency is caused by mutations in the OCTN2 gene.

Moreover, due to the close relationship of OCTN2 gene mutation and systemic carnitine deficiency, the Inventors found that this disease can be tested by examining whether or not there is a mutation in the OCTN2 gene of a patient.

It was also found that systemic carnitine deficiency could be treated by using the normal OCTN2 gene and its protein, to complete the invention.

Therefore, this invention relates to molecules used in the testing and treatment of systemic carnitine deficiency, as well as methods for testing the disease. More specifically, the present invention relates to:

(1) a DNA for testing systemic carnitine deficiency, wherein the DNA hybridizes to a DNA comprising the nucleotide sequence of SEQ ID NO:5, or the transcription regulatory region thereof, and comprises at least 15 nucleotides;

(2) a molecule as in any one of (a) to (c) below, which is used for the treatment of systemic carnitine deficiency,
   (a) a protein comprising the amino acid sequence of SEQ ID NO:1,
   (b) a compound that promotes the activity of the protein comprising the amino acid sequence of SEQ ID NO:1, or,
   (c) a DNA encoding the protein comprising the amino acid sequence of SEQ ID NO:1;

(3) a pharmaceutical composition for treating systemic carnitine deficiency, comprising a molecule of (2) as the active ingredient;

(4) a pharmaceutical composition for treating systemic carnitine deficiency, comprising an antibody binding to the protein comprising the amino acid sequence of SEQ ID NO:1 as the active ingredient;

(5) a test method for systemic carnitine deficiency comprising the detection of a mutation in the DNA encoding the protein comprising the amino acid sequence of SEQ ID NO:1, or the transcription regulatory region of said DNA;

(6) the test method for systemic carnitine deficiency of (5) comprising the steps of,
   (a) preparing a DNA sample from a patient,
   (b) amplifying patient-derived DNA using the DNA of (1) as a primer,
   (c) cleaving the amplified DNA,
   (d) separating the DNA fragments by their size,
   (e) hybridizing the DNA of (1) labeled by a detectable label as a probe to the DNA fragments separated, and,
   (f) comparing the size of the DNA fragment detected with a control from a healthy individual, (7) the test method for systemic carnitine deficiency of (5) comprising the steps of,
   (a) preparing an RNA sample from a patient,
   (b) separating the prepared RNA by size,
   (c) hybridizing the DNA of (1) labeled by a detectable label as a probe to the RNA fragments separated, and,
   (d) comparing the size of the RNA fragment detected with a control from a healthy individual, (8) the test method for systemic carnitine deficiency of (5) comprising the steps of, (a) preparing a DNA sample from a patient, (b) amplifying patient-derived DNA using the DNA of (1) as a primer, (c) dissociating the amplified DNA to single-stranded DNA, (d) separating the dissociated single-stranded DNA on a non-denaturing gel, and, (e) comparing the mobility of separated single stranded DNA on the gel with a control from a healthy individual, (9) the test method for systemic carnitine deficiency of (5) comprising the steps of, (a) preparing a DNA sample from a patient, (b) amplifying patient-derived DNA using the DNA of (l) as a primer, (c) separating the amplified DNA on a gel in which the concentration of the DNA denaturant gradually increases, and, (d) comparing the mobility of separated DNA on the gel with a control from a healthy individual.

The present invention is based on the finding by the present inventors that systemic carnitine deficiency is caused by a mutation in the gene named "OCTN2". First and foremost, this invention relates to a molecule used in the testing and treatment of systemic carnitine deficiency, as well as a method for testing the disease.

In the present invention, the genomic DNA region (for example, SEQ ID NO:5) containing OCTN2, or an oligonucleotide (probe and primer) that hybridizes to the nucleotide sequence of the regulatory region (comprising the intron, promoter, and enhancer sequences as well) of OCTN2 is used.

This oligonucleotide preferably hybridizes specifically to the genomic DNA region containing OCTN2, or the regulatory region of OCTN2. Herein, "hybridizes specifically" indicates that cross-hybridization does not significantly occur with DNA encoding other proteins, under normal hybridizing conditions, preferably under stringent conditions (for example, the conditions in Sambrook et al., Molecular Cloning second edition, Cold Spring Harbor Laboratory Press, New York, USA, 1989).

When using as a primer, the oligonucleotide is usually, 15 to 100 bp, preferably, 17 to 30 bp. The primer may be any, as long as it can amplify at least a part of the OCTN2 gene or the region regulating its expression. Such regions comprise, for example, the exon region of OCTN2, the intron region, the promoter region, and enhancer region.

On the other hand, the oligonucleotide used as a probe usually comprises at least 15 bp or more if it is a synthetic oligonucleotide. It is also possible to use a double stranded DNA obtained from a clone incorporated into a vector such as plasmid DNA. The probe may be any, as long as it specifically hybridizes to at least a part of the OCTN2 gene or the region regulating the expression of the gene. Regions to which the probe hybridizes include, for example, the exon region, intron region, promoter region, and enhancer region of the OCTN2 gene. When using as the probe, oligonucleotide or double stranded DNA is suitably labeled. Examples of labeling methods are, phosphorylating the 5' end of the oligonucleotide by $^{32}$P using T4 polynucleotide kinase, and incorporating a substrate nucleotide labeled by an isotope such as $^{32}$P, a florescent dye, or biotin, using the random hexamer oligonucleotide as a probe and using DNA polymerase such as the Klenow enzyme (random priming technique).

In the present invention, "a test method for systemic carnitine deficiency" includes not only a test for patients showing symptoms of systemic carnitine deficiency caused by a mutation of the OCTN2 gene, but also a test for detecting a mutation of the OCTN2 gene for determining whether or not the person tested is likely to develop systemic carnitine deficiency arising from a OCTN2 gene mutation. In other words, the risk of developing systemic carnitine deficiency may greatly increase in cases where one of the OCTN2 alleles develops a mutation, even when no symptoms are visible on the outside. Therefore, tests for specifying patients (carriers) having a mutation in an OCTN2 allele are also included in the invention.

In the present invention, a test method for systemic carnitine deficiency using the above oligonucleotides comprises the detection of a mutation in the OCTN2 gene or its transcription regulatory region. One embodiment of this method of testing is the direct determination of the nucleotide sequence of the patient's OCTN2 gene. For example, using the above oligonucleotide as the primer, the whole OCTN2 gene or a part of it is amplified by the Polymerase Chain Reaction (PCR) using as the template a DNA isolated from a patient suspected of having a disease caused by an OCTN2 mutation. By comparing this sequence with that of a healthy individual, it is possible to conduct a test for a disease arising from an OCTN2 gene mutation.

As the testing method of the invention, other than determining the nucleotide sequence of DNA derived directly from the patient, several other methods are also used. One such embodiment comprises the following steps of: (a) preparing a DNA sample from a patient; (b) amplifying the patient-derived DNA using the primer of this invention; (c) dissociating amplified DNA into single-stranded DNA; (d) separating the dissociated single-stranded DNA on a non-denaturing gel; and, (e) comparing the mobility of separated single stranded DNA on the gel with a control from a healthy individual.

An example of such a method is the PCR-single-strand conformation polymorphism (PCR-SSCP) method (Cloning and polymerase chain reaction-single-strand conformation polymorphism analysis of anonymous Alu repeats on chromosome 11, Genomics, 1992 Jan. 1, 12(1):139-146; Detection of p53 gene mutations in human brain tumors by single-strand conformation polymorphism analysis of polymerase chain reaction products, Oncogene, 1991 Aug. 1, 6(8):1313-1318; Multiple fluorescence-based PCR-SSCP analysis with postlabeling, PCR Methods Appl. 1995 Apr. 1, 4(5):275-282). This method is comparatively easy to handle, and has various advantages such as requiring only a small amount of a sample, and therefore, is suitable for screening a large number of DNA samples. The principle of this method is as follows. When a double stranded DNA fragment is disassociated into single strands, each strand forms an original high-order structure depending on its nucleotide sequence. When these dissociated DNA strands are electrophoresed within a polyacrylamide gel free of denaturants, the single stranded DNAs that are complementary and have the same length, migrate to different positions according to the difference in their high-order structure. This high order structure of the single strands change even by a single nucleotide substitution showing different mobilities in polyacrylamide gel electrophoresis. Therefore, the presence of a mutation in a DNA fragment due to point mutation, deletion, or insertion can be detected by the change in mobility.

Specifically, first, the whole OCTN2 gene or a part of it is amplified by PCR, and such. A length of 200 to 400 bp is usually preferred amplified range. Regions amplified include all the exons and all the introns of the OCTN2 gene, as well as the promoter and enhancer of the OCTN2 gene. PCR can be done, for example, according to conditions described in Example 1. When amplifying the gene fragment by PCR, a primer labeled by an isotope such as $^{32}$P, a fluorescent dye, or biotin is used, or the DNA fragment synthesized by PCR after adding a substrate nucleotide labeled by an isotope such as $^{32}$P, a fluorescent dye, or biotin, is labeled. Labeling can also be done by adding to the synthesized DNA fragment a substrate nucleotide labeled by an isotope such as $^{32}$P, a fluorescent dye, or biotin, using the Klenow enzyme and such after the PCR reaction. The labeled DNA fragment thus obtained is denatured by heating and such, and electrophoresed in a polyacrylamide gel free of denaturants such as urea. Conditions for separating the DNA fragment can be improved by adding a suitable amount (about 5 to 10%) of glycerol to the polyacrylamide gel. Conditions of electrophoresis vary depending on the properties of the DNA fragment, but room temperature (from 20 to 25° C.) is usually used. When a preferable separation cannot be accomplished, the temperature that gives the optimum mobility at 4 to 30° C. is evaluated. Following electrophoresis, the mobility of the DNA fragment is detected by an autoradiography using X-ray films, a scanner that detects fluorescence, and so on, and analyzed. When a band having a difference in mobility is detected, this band is directly excised from the gel, re-amplified by PCR, and is directly sequenced to verify the presence of a mutation. Even when labeled DNA is not used, the band can be detected by staining the gel after electrophoresis with ethidium bromide, silver, and such.

Another embodiment of the test method of the present invention comprises the following steps of: (a) preparing a DNA sample from a patient; (b) amplifying patient-derived DNA using the primer of this invention; (c) cleaving the amplified DNA; (d) separating the DNA fragments according to their size; (e) hybridizing the probe DNA of the invention labeled with a detectable label to the DNA fragments separated; and (f) comparing the size of the detected DNA fragment with a control from a healthy individual.

Such methods include those using Restriction Fragment Length Polymorphism (RFLP), PCR-RFLP method, and so on. Restriction enzymes are usually used to cleave DNA. Specifically, compared to a DNA fragment of a healthy individual, the size of one obtained following restriction enzyme treatment changes when a mutation exists at the recognition site of the restriction enzyme, or when nucleotides have been inserted or deleted in the DNA fragment resulting from restriction enzyme treatment. The portion containing the mutation is amplified by PCR, the amplified products are treated with each restriction enzyme and electrophoresed to detect the mutation as the difference of mobility. Alternatively, chromosomal DNA is cleaved with these restriction enzymes, and after electrophoresis, the presence or absence of a mutation can be detected by southern-blotting using the probe DNA of the invention. The restriction enzymes used can be suitably selected according to each mutation. This method can use not only genomic DNA, but also cDNA made by treating RNA prepared from patients with reverse transcriptase, cleaving this cDNA as-it-is with restriction enzymes, and then conducting southern blotting. It is also possible to examine the changes in mobility after amplifying the whole OCTN2 gene, or a part of it, by PCR using the above cDNA as the template, and cleaving the amplified products by restriction enzymes.

A similar detection is also possible using RNA prepared from patients instead of DNA. This method includes the steps of: (a) preparing an RNA sample from a patient; (b) separating the prepared RNA according to their size; (c) hybridizing the probe DNA of the invention labeled by a detectable label to the separated RNA; and (d) comparing the size of the detected RNA with a control from a healthy individual. In a specific example of this method, RNA prepared from a patient is electrophoresed, northern blotting is done using the probe of the invention to detect the mobility change.

Another embodiment of the method of the invention comprises the steps of: (a) preparing a DNA sample from a patient; (b) amplifying patient-derived DNA using the primer of this invention; (c) separating the amplified DNA on a gel in which the concentration of the DNA denaturant gradually increases; and, (d) comparing mobility of the DNA separated upon the gel with a control from a healthy individual.

An example of such a method is denaturant gradient gel electrophoresis (DGGE). The whole OCTN2 gene or a part of it is amplified by a method such as PCR using the primer of the invention, and the amplified product is electrophoresed in a gel in which the concentration of the DNA denaturant gradually increases, and compared with a control from a healthy individual. In the case of a DNA having a mutation, the DNA fragment will become single stranded at a low denaturant concentration and the moving speed will become extremely slow. The presence or absence of a mutation can be detected by detecting the change in mobility.

Allele Specific Oligonucleotide (ASO) hybridization can be used alternatively when the aim is to detect a mutation at a specific site. When an oligonucleotide comprising a nucleotide sequence thought to have a mutation is prepared and this is hybridized with sample DNA, the hybrid formation efficiency will decrease when there is a mutation. This can be detected by southern blotting and by a method using the property of special fluorescent reagents that quench when intercalated into a hybrid gap. The detection by ribonuclease A mismatch cleavage method can also be used. Specifically, the whole OCTN2 gene, or a part of it, is amplified by a method such as PCR, and the amplified product is hybridized to labeled RNA prepared from OCTN2 cDNA and such incorporated into a plasmid vector, etc. The hybrids will be single stranded in the portion where a mutation exists. This portion is cleaved by ribonuclease A and the existence of a mutation can be detected by autoradiography, and such.

The present invention also relates to a test drug for systemic carnitine deficiency that comprises an antibody binding to the OCTN2 protein as the active ingredient. An antibody binding to the OCTN2 protein can be prepared using methods well known to those skilled in the art. Polyclonal antibodies can be made by, obtaining the serum of small animals such as rabbits immunized with the OCTN2 protein (apart from the natural protein, recombinant OCTN2 proteins expressed in suitable host cells (*E. coli*, yeasts, mammals, and such), such as recombinant OCTN2 protein expressed in *E. coli* as a fusion protein with GST) of the present invention, or a partial peptide. The serum is then purified by, for example, ammonium sulfate precipitation, protein A or protein G column chromatography, DEAE ion exchange chromatography, or an affinity chromatography using a column to which the protein of the present invention or synthetic peptide is coupled. Monoclonal antibodies can be made by immunizing small animals such as mice with the OCTN2 protein or a partial peptide thereof, excising the spleen from the mouse, homogenizing it and separating cells, fusing the cells with mouse myeloma cells using a reagent such as polyethylene glycol, and selecting clones that produce an antibody binding to the OCTN2 protein from the fused cells (hybridomas) produced. Next, the obtained hybridomas are transplanted into the abdominal cavity of a mouse, and ascites are extracted from the mouse. The obtained monoclonal antibodies can be purified by, for example, ammonium sulfate precipitation, protein A or protein G column chromatography, DEAE ion exchange chromatography, or an affinity chromatography using a column to which the OCTN2 protein or synthesized peptide is coupled.

When using the antibody as a test drug, it is mixed with sterile water, physiological saline, plant oils, surfactants, lipids, solubilizers, stabilizers (BSA, gelatin, etc.), preservatives, and such, according to needs. An example of a test for systemic carnitine deficiency features the staining of tissues collected or cells isolated from a patient by the enzyme-labeled antibody method, fluorescence-labeled antibody method, and test for a deficiency, abnormal accumulation, or abnormal intracellular distribution of the OCTN2 protein. Testing can also be done by preparing a cell-extract of tissues collected or cells isolated from a systemic carnitine deficiency patient, separating the cell-extract by methods such as SDS-PAGE, transferring onto a nitrocellulose membrane, PVDF membrane, and such, and then staining this by a method (western blotting, immunoblotting, etc) using the above-described enzyme-labeled antibody method, etc.

The present invention also relates to a therapeutic drug for systemic carnitine deficiency. One such embodiment has the OCTN2 gene as the active ingredient. When using the OCTN2 gene as a therapeutic drug, it is given to the patient by oral, intravenous, topical administration and such, as the full length OCTN2 chromosomal DNA, a part of it, or by incorporating the OCTN2 DNA into a suitable vector, for example, adenovirus vector, adeno associated virus vector, retro virus vector, or plasmid DNA. The ex vivo method can also be used for administration apart from the in vivo method. The transition and absorption into tissues can be enhanced by enclosing the gene in a liposome prepared by micellization of phospholipids, or by adding a cationic lipid and forming a complex with genomic DNA. Therefore, the method of the invention can replace a patient's mutated OCTN2 gene by a normal gene, and also additionally administer the normal gene, thereby enabling the treatment of systemic carnitine deficiency.

Another embodiment of the invention relating to a therapeutic drug of systemic carnitine deficiency comprises the OCTN2 protein as the active ingredient. The amino acid sequences of human and mouse OCTN2 proteins are shown in SEQ ID NOs:1 and 3, respectively. The OCTN2 protein can be prepared as a natural protein and also as a recombinant protein. The natural protein can be prepared by a method well known to one skilled in the art, for example, by isolating the OCTN2 protein from tissues or cells that show a high level expression of the protein (e.g. fetal kidney) by affinity chromatography using an antibody against a partial peptide of the OCTN2 protein. On the other hand, a recombinant protein can be prepared by culturing cells transformed by DNA (for example, SEQ ID NO:2) encoding the OCTN2 protein. Cells used for the production of recombinant proteins include mammalian cells such as, COS cells, CHO cells, and NIH3T3 cells, insect cells such as sf9 cells, yeast cells, and *E. coli* cells. Vectors for expressing the recombinant proteins within cells vary according to the host used, and normally, pcDNA3 (Invitrogen), pEF-BOS (Nucleic Acids Res. 1990, 18(17), 5322) and such are used as vectors for mammalian cells, the "BAC-to-BAC baculovirus expression system" (GIBCO BRL) and such are used for insect cells, "Pichia Expression Kit" (Invitrogen) and such are used for yeast cells, pGEX-5X-1 (Pharmacia), "QIAexpress system" (Qiagen) and such are used for *E. coli* cells. Vectors are introduced to hosts using, for example, the calcium phosphate method, DEAE dextran method, method using cationic liposome DOTAP (Boehringer Mannheim), and Superfect (Qiagen), electroporation method, calcium chloride method, and such. The recombinant protein can be purified from the transformant obtained usually using methods described in "The Qiaexpressionist handbook, Qiagen, Hilden, Germany".

When using the obtained OCTN2 protein as a therapeutic drug for treating systemic carnitine deficiency, the OCTN2 protein can be directly administered, or can be given after being formulated into a pharmaceutical composition by a well-known pharmaceutical manufacturing method. For example, the drug can be given after suitably combining with a generally used carrier or medium such as, sterilized water, physiological saline, plant oils, surfactants, lipids, solubilizers, stabilizers, preservatives, and such.

The dosage varies depending on factors such as the patient's body weight, age, healthiness, and method of administration, but a skilled artisan can suitably select the dosage. Usually, it is within the range from 0.01 to 1000 mg/kg. The administration can be done orally, intravenously, intramuscularly, or percutaneously. A skilled artisan can easily replace, add, or delete amino acid(s) in the amino acid sequence of the OCTN2 protein using a well-known method such as the site-specific mutation induction system using PCR (GIBCO-BRL, Gaithersburg, Maryland), site-specific mutagenesis using oligonucleotides (Kramer, W. and Fritz, H J, 1987, Methods in Enzymol, 154:350-367), the Kunkel method (Methods Enzymol., 1988, 85:2763-2766), and such.

Another embodiment of the therapeutic drug for systemic carnitine deficiency uses a compound that enhances the activity of the OCTN2 protein as the active ingredient. Such a compound can be screened as follows. For example, a plasmid expressing the OCTN2 protein is constructed, and this is introduced into HEK293 cells by the calcium phosphate method. Radiolabeled carnitine and a test compound are added to this transformant and the carnitine transporting activity into the cells is determined. A compound that can enhance the carnitine transporting activity is selected by comparing with the activity of the OCTN2 protein in the absence of the test compound. See Japanese Patent Application Hei 9-260972 and Hei 10-156660 for the detailed method.

Similar to the above-mentioned use of the OCTN2 protein as a therapeutic drug, the isolated compound can also be formulated into a pharmaceutical composition using well-known pharmaceutical manufacturing methods. The dose range is usually within 0.01 to 1000 mg/kg.

It is also conceivable to utilize the region regulating OCTN2 gene expression or a factor that binds to this region for the treatment of systemic carnitine deficiency.

The OCTN2 gene comprising the region that regulates OCTN2 gene expression is useful in the above-mentioned gene therapy as it can express the OCTN2 gene under normal expression regulation in vivo by introducing it into patients who lack the OCTN2 gene, or who have a defect in OCTN2 gene expression.

Moreover, if the promoter site is determined from the upstream region of the OCTN2 gene, a compound that regulates OCTN2 gene expression amount can be simply screened by using a reporter gene expression vector having the above promoter site through examining the influence of various compounds on the production of reporter gene products. Such a screening method comprises the following steps of, (a) constructing a vector in which a reporter gene is ligated to the downstream of the promoter site, (b) introducing the vector into a suitable cell, and, (c) detecting the reporter gene activity by contacting or introducing a test compound to the above cell. Examples of the test compound include, proteins, peptides, synthetic compounds, natural compounds, genes, gene products, and such.

A compound regulating OCTN2 gene expression can also be screened by contacting a test sample with the promoter site, and selecting a compound (such as a protein) that binds to the promoter site. For example, a synthetic oligo DNA and such having the nucleotide sequence of the promoter site is prepared, this is bound to a suitable support such as Sepharose, and contacted with a cell-extract, and such. Then, a transcription factor and such that binds to this promoter site and regulates OCTN2 gene expression can be purified by, for example, affinity chromatography.

DETAILED DESCRIPTION OF THE INVENTION

Figure 1:
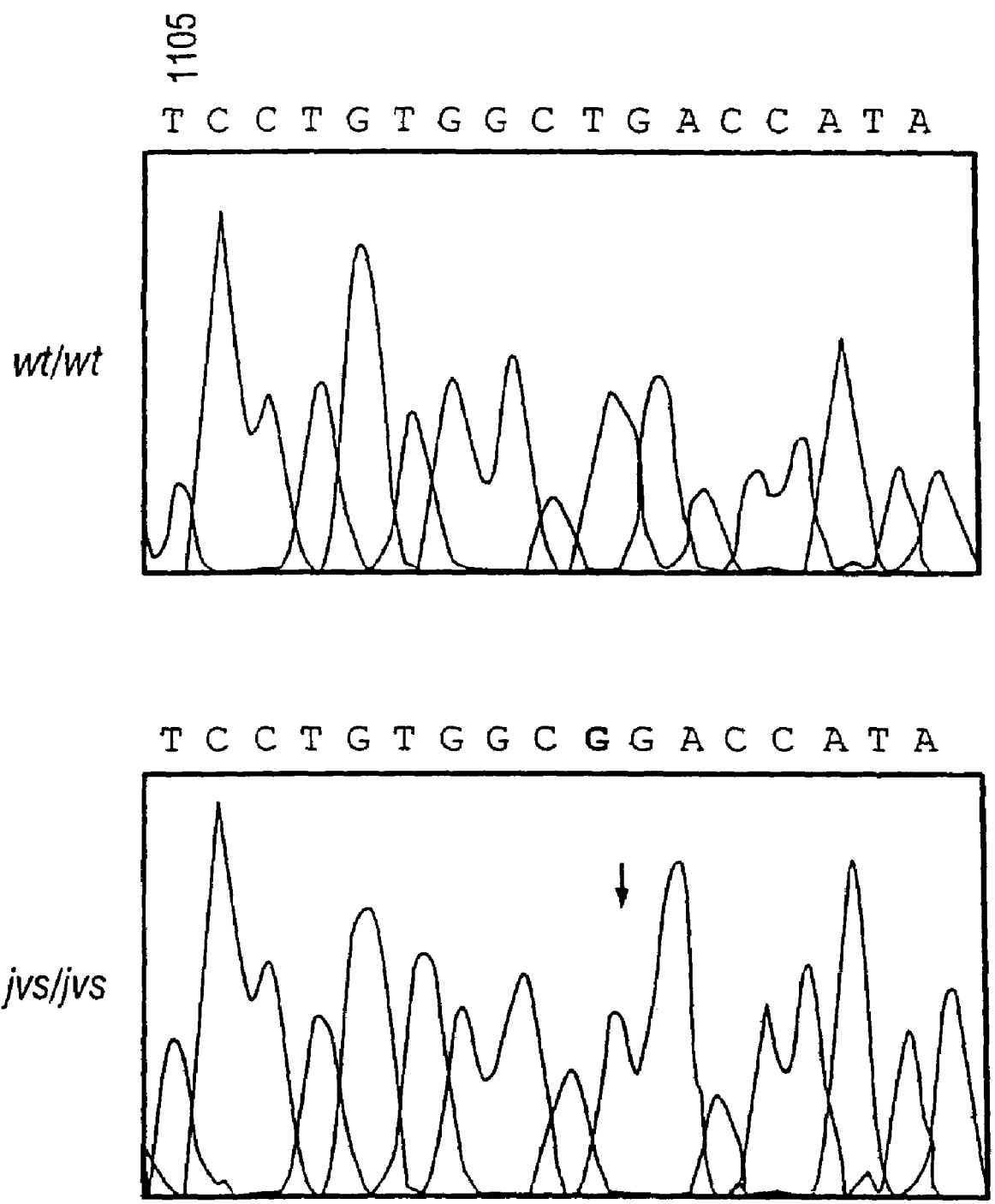
FIG. 1 shows the direct sequencing of the mouse OCTN2 gene amplified by RT-PCR. wt/wt shows wild-type homologous mouse (SEQ ID NO:27), and jvs/jvs shows the jvs homologous mouse (SEQ ID NO:28). OCTN2 gene of the jvs mouse has a mutation at the nucleotide shown by the arrow.

The invention shall be described in detail below, but it is not to be construed as being limited thereto.

EXAMPLE 1

Proof in Mouse and Human Showing that the Gene Responsible for Systemic Carnitine Deficiency (SCD) is OCTN2

The Inventors have previously isolated human cDNA encoding a protein having an activity to transport carnitine in a sodium-ion dependent manner, and also the corresponding mouse cDNA (Japanese Patent Application No. Hei 9-260972, Japanese Patent Application No. Hei 10-156660). The nucleotide sequences of the human and mouse OCTN2 cDNA isolated by the Inventors are shown in SEQ ID NO:2 and 4, respectively, and the amino acid sequences of the proteins encoded by these cDNAs are shown in SEQ ID NO:1 and 3, respectively.

The Inventors drew up a working hypothesis that OCTN2 might be the gene responsible for systemic carnitine deficiency, and conducted experiments to prove this.

(1) OCTN2 Gene Analysis in Juvenile Visceral Steatosis (jvs) Mouse

The juvenile visceral steatosis (jvs) mouse was generated due to a mutation in the C3H.OH mouse. This jvs mouse shows symptoms similar to systemic carnitine deficiency patients, and shows an extremely low carnitine concentration within its blood and tissues. This phenotype is inherited by autosomal inheritance. From the above facts, the jvs mouse is considered to be a mouse model for systemic carnitine deficiency (Hashimoto, N. et al., Gene-dose effect on carnitine transport activity in embryonic fibroblasts of JVS mice as a model of human carnitine transporter deficiency, Biochem Pharmacol, 1998, 55:1729-1732). The Inventors examined the OCTN2 gene arrangement of the jvs mouse. Specifically, whole RNA was extracted from the kidney of a jvs homologous mouse, cDNA was synthesized, jvs mouse OCTN2 cDNA was amplified using this synthesized cDNA as the template by RT-PCR, and the sequence was examined by direct sequencing.

The amplification reaction by PCR was conducted as follows. For the 5' side fragment, the primers MONB 31 (5'-gataagcttacggtgtccccttattcccatacg-3'/SEQ ID NO:22) and MONB 20 (5'-cccatgccaacaaggacaaaaagc-3'/SEQ ID NO:23) were prepared. Then, amplification was done within a reaction solution (50 µl) containing, cDNA, 5 µl of 10×KOD buffer (Toyobo), 5 µl of 2 mM dNTPs, 2 µl of 25 mM MgCl$_2$, 0.5 µl of KOD DNA polymerase (Toyobo), 1 µl of 20 µM MONB 31 primer, and 1 µl of 20 µM MONB 20 primer at 94° C. for 3 min, 30 cycles of "94° C. for 30 sec, 50° C. for 30 sec, and 74° C. for 1 min", and 72° C. for 10 min. As for the 3' side fragment, the primers MONB 6 (5'-tgtttttcgtgggtgtgctgatgg-3'/SEQ ID NO:24) and MONB 26 (5'-acagaacagaaaagccct-cagtca-3'/SEQ ID NO:25) were prepared, and amplification was done within a reaction solution (50 µl) containing cDNA, 5 µl of 10×ExTaq buffer (TaKaRa), 4 µl of 2.5 mM dNTPs, 1 µl of a mixture of ExTaq DNA polymerase (TaKaRa) and anti Taq antibody (TaqStart antibody™, CLONTECH), 1 µl of 20 µM MONB 6 primer, and 1 µl of 20 µM MONB 26 primer, at 94° C. for 2 min, 30 cycles of "94° C. for 30 sec, 60° C. for 30 sec, and 74° C. for 2 min", and 72° C. for 10 min.

Figure 2:
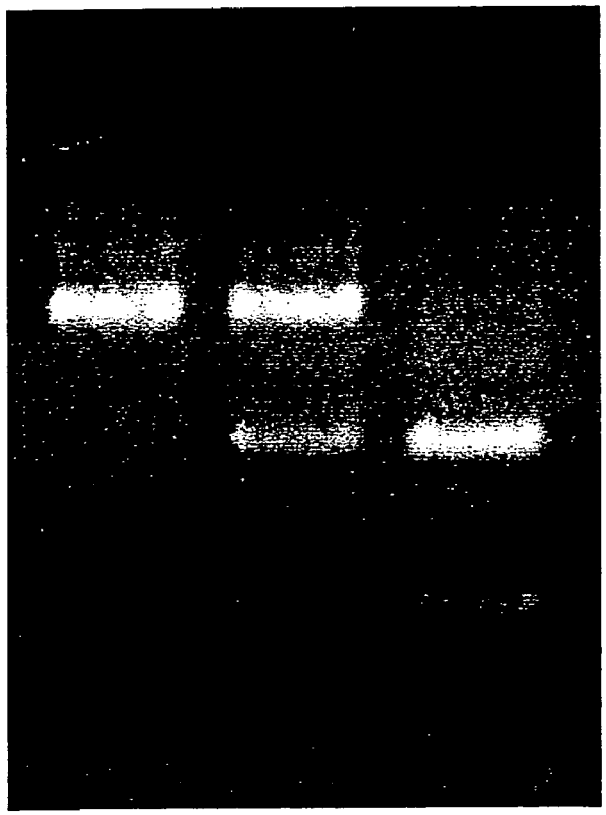
FIG. 2 is electrophoretic images showing the mutation in the OCTN2 gene of the jvs mouse, which was detected using the PCR-RFLP method (Cfr 131 cleavage). The fragment shown by the arrow head derives from the normal gene, and the fragments shown by the arrows were due to the mutated gene.
Figure 2:
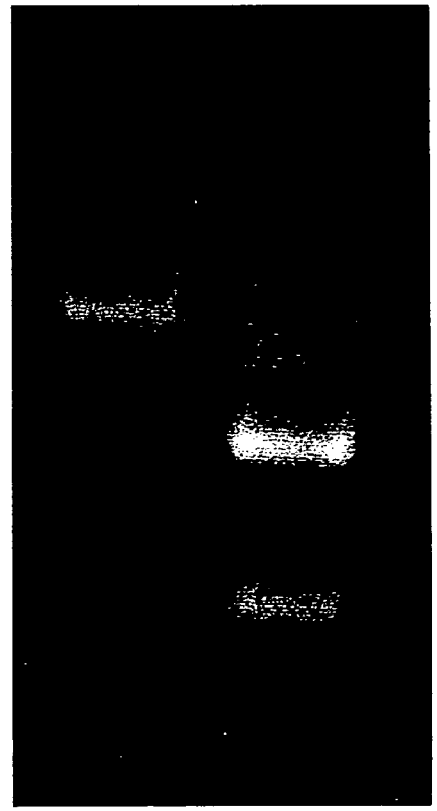

Sequencing revealed that the codon encoding the 352$^{nd}$ leucine (CTG) was mutated to a codon encoding arginine (CGG) (FIG. 1). This mutation can be detected by Restriction Fragment Length Polymorphism (PCR-RFLP) due to the presence of the Cfr13I restriction enzyme site. This method revealed that the jvs homologous mouse (jvs/jvs) had this mutation in both alleles, and that the heterologous mouse (wt/jvs) has both the mutated and wild type alleles (FIG. 2 left). This mutation was also found in the C57BL jvs mouse in which the genetic background has been replaced with that of the C57BL/6 mouse by backcrossing 12 times or more (FIG. 2 right). Since the C57BL jvs mouse was constructed after a series of selections using the jvs phenotype as an index, the jvs phenotype and OCTN2 mutations are considered to be very closely associated.

Figure 3:
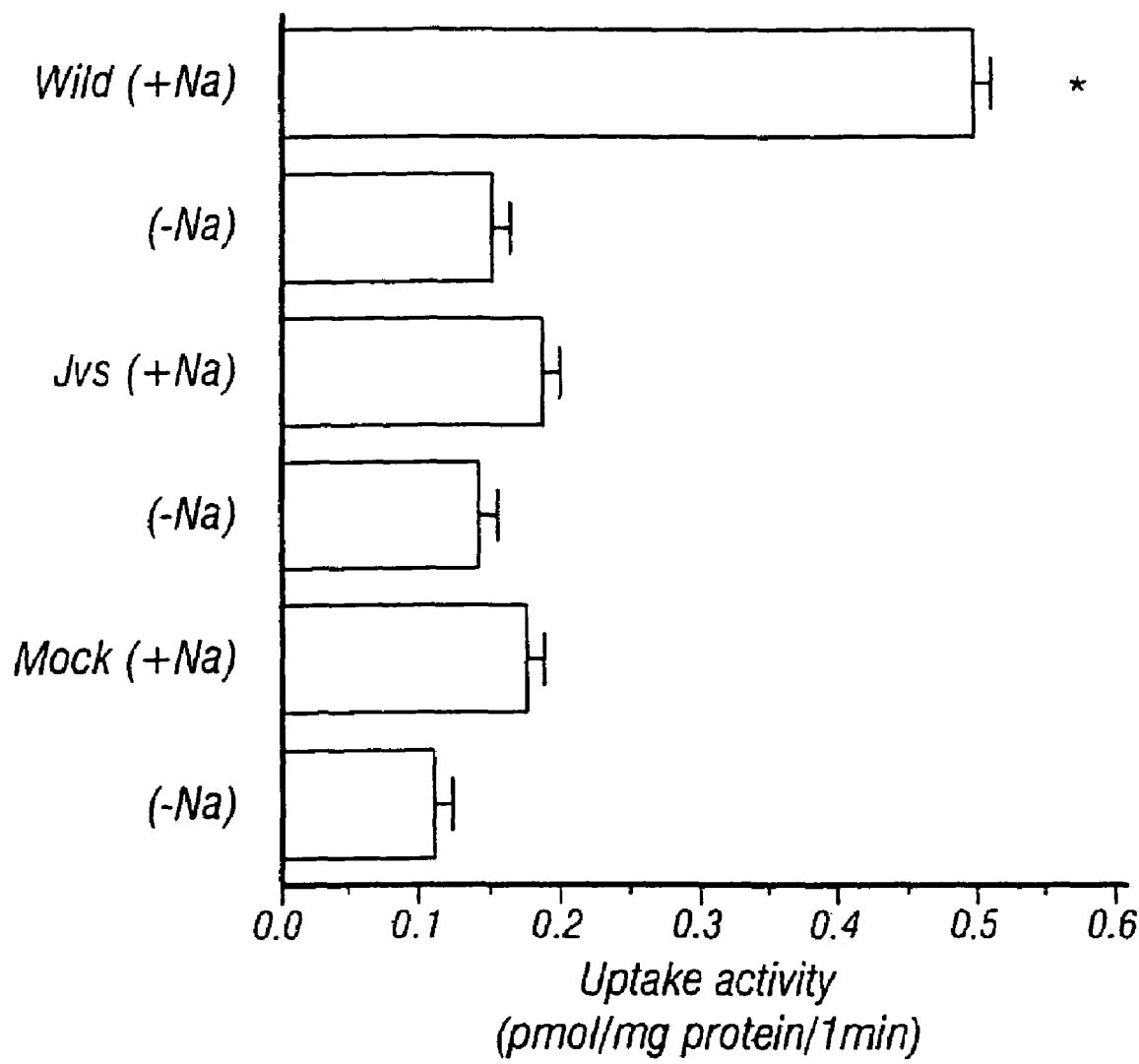
FIG. 3 shows results of the carnitine transporting activity assay of wild-type mouse OCTN2 and the mutant mouse OCTN2. A sodium-dependent carnitine transporting activity is seen for the wild type, whereas the mutant (Jvs) shows absolutely no activity. "Mock" is when a cDNA-non-containing vector was used as the control.
Figure 4:
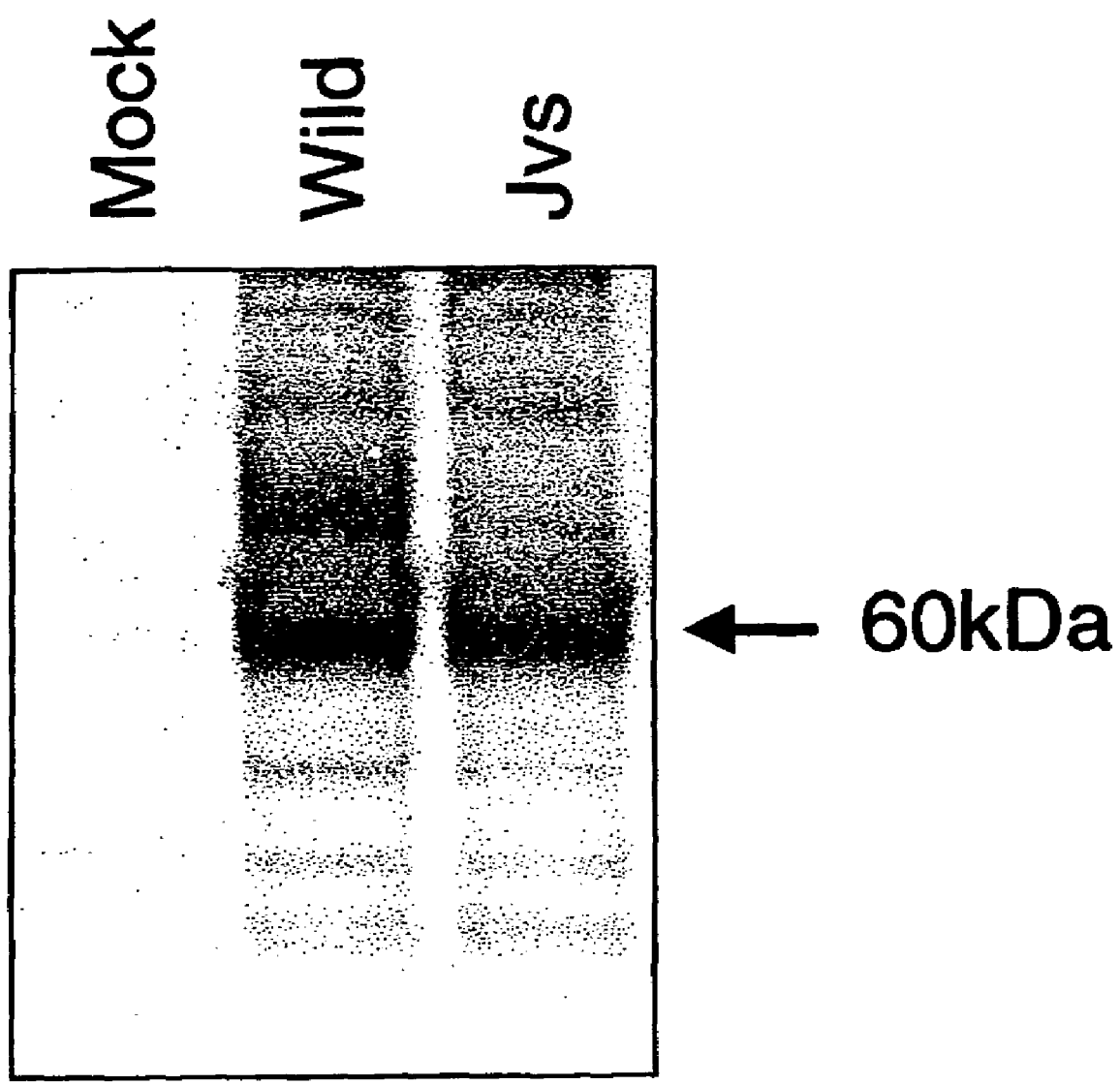
FIG. 4 is an electrophoretic image showing the results of western blot analysis using anti myc antibody. It can be seen that the wild-type OCTN2 protein (wild) and the mutant OCTN2 protein (Jvs) is produced in similar amounts. "Mock" is when a cDNA-non-containing vector was used as the control.

Next, the effect this mutation has on the carnitine transporting activity was examined. Plasmid DNA expressing wild-type mouse OCTN2, and those expressing mutated OCTN2 were separately introduced into HEK293 cells, and then, carnitine transporting ability was measured similar to the assay of human OCTN2 described in Japanese Patent Application Hei 10-156660 (FIG. 3). This revealed that although wild-type mouse OCTN2 shows a carnitine transporting activity similar to human OCTN2, the mutated OCTN2 has absolutely no activity. However, both proteins were confirmed to be expressed at a similar amount by a western blotting using an antibody against the c-myc epitope sequence (NH2-EQKLISEEDL-COOH; SEQ ID NO:26) added to the C terminus (FIG. 4).

Thus, the jvs mouse is thought to have developed the disease due to a functional deletion mutation of the OCTN2 gene.

(2) OCTN2 Gene Analysis in Human Systemic Carnitine Deficiency Patients

A database search using human OCTN2 cDNA sequence revealed that the human OCTN2 genomic DNA sequence has been decoded by Lawrence Berkeley National Laboratory (LBNL) of the United States as a part of the human genome project. However, it was only recorded as several cosmid clone sequences, therefore, the inventors determined a complete human OCTN2 genomic DNA sequence (SEQ ID NO:5) by comparing with human OCTN2 cDNA sequence and suitably combining the clone sequences. The human OCTN2 gene is an about 26 kb gene comprising ten exons and nine introns. The eight pairs of primers shown below, which can amplify all the exons as eight fragments, were prepared from this gene arrangement.

Specifically, OCN2 43 (5'-GCAGGACCAAGGCGGCG-GTGTCAG-3', SEQ ID NO:6) and OCN2 44 (5'-AGACTA-GAGGAAAAACGGGATAGC-3', SEQ ID NO:7) for exon one; OCN2 25 (5'-AGATTTTTAGGAGCAAGCGTTAGA-3' SEQ ID NO:8) and OCN2 26 (5'-GAGGCAGACAC-CGTGGCACTACTA-3', SEQ ID NO:9) for exon two; OCN2 27 (5'-TTCACACCCACTTACTGGATGGAT-3' SEQ ID NO:10) and OCN2 50 (5'-ATTCTGTTTTGTTTTG-GCTCTTTT-3', SEQ ID NO:11) for exons three and four; OCN2 31 (5'-AGCAGGGCCTGGGCTGACATAGAC-3', SEQ ID NO:12) and OCN2 32 (5'-AAAGGACCTGACTC-CAAGATGATA-3', SEQ ID NO:13) for exon five; OCN2 33 (5'-TCTGACCACCTCTTCTTCCCATAC-3', SEQ ID NO:14) and OCN2 34 (5'-GCCTCCTCAGCCACTGTCGG-TAAC-3', SEQ ID NO:15) for exon six; OCN2 35 (5'-ATGT-TGTTCCTTTTGTTATCTTAT-3', SEQ ID NO:16) and OCN2 36 (5'-CTTGTTTTCTTGTGTATCGTTATC-3', SEQ ID NO:17) for exon seven; OCN2 37 (5'-TAT-GTTTGTTTTGCTCTCAATAGC-3', SEQ ID NO:18) and OCN2 40 (5'-TCTGTGAGAGGGAGTTTGCGAGTA-3', SEQ ID NO:19) for exon eight and nine; and, OCN2 41 (5'-TACGACCGCTTCCTGCCCTACATT-3', SEQ ID NO:20) and OCN2 42 (5'-TCATTCTGCTCCATCTTCAT-TACC-3', SEQ ID NO:21) for exon 10.

Next, human OCTN2 gene mutations in three families that have systemic carnitine deficiency patients, but no blood relationships were examined. The analysis is done by amplifying all the exons using the above primers and genomic DNA prepared from blood cells as the template, and subjecting the amplified products into direct sequencing.

The amplification reaction by PCR was done within a reaction solution (50 µl) containing 100 ng of genomic DNA, 5 µl of 10×ExTaq buffer (TaKaRa), 4 µl of 2.5 mM dNTPs, 1 µl of a mixture of ExTaq DNA polymerase (TaKaRa) and anti Taq antibody (TaqStart antibody™, CLONTECH), and 1 µl of each of the 20 µM primers. The reaction conditions were, 94° C. for 2 min, 36 cycles of "94° C. for 30 sec, 60° C. for 30 sec, and 74° C. for 2 min", and 72° C. for 10 min. However, in the case of exon one and exon five amplification, a reaction solution (50 µl) containing 100 ng genomic DNA, 25 µl of 2×GC buffer 1 (TaKaRa), 8 µl of 2.5 mM dNTPs, 0.5 µl of LA Taq DNA polymerase (TaKaRa), and 1 µl of each of the 20 µM primers, was used.

Figure 5:
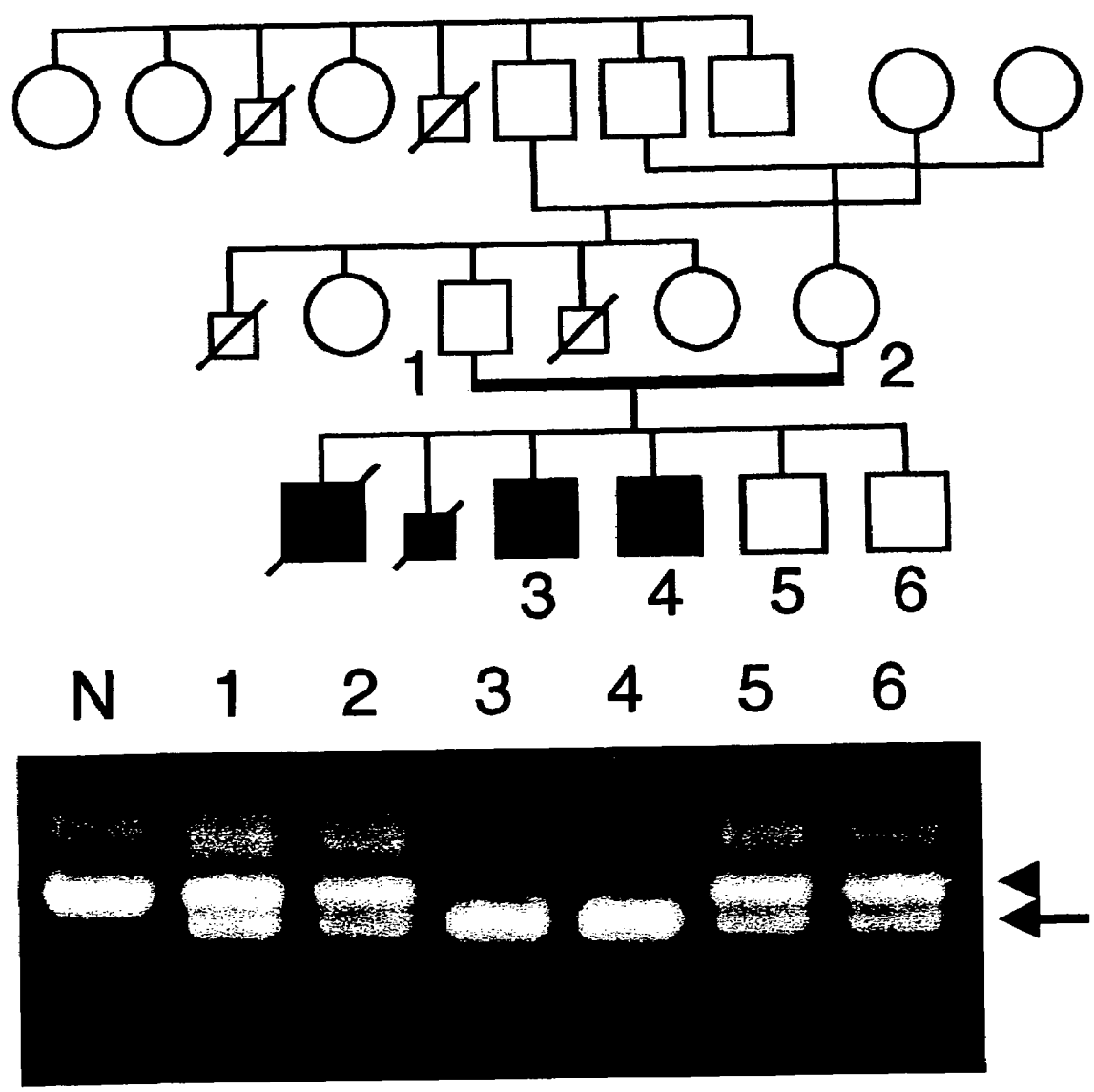
FIG. 5 shows the results of OCTN2 gene analysis in the KR family. The pedigree chart of this family is shown on top. Squares indicate males, circles females, filled ones individuals having systemic carnitine deficiency, and crossed squares indicate deceased individuals. An electrophoretic image showing the PCR results is given below. "N" shows the results of the normal gene used as the control. The fragments shown by the arrowhead are PCR products derived from the normal gene, and the fragments shown by the arrow derived from the gene where the defect exits.

In the first family (KR family), a 113 bp deletion was found in first exon of the OCTN2 gene of a systemic carnitine deficiency patient (FIG. 5). This deletion affects the initiation codon and thus, a complete protein will not be produced. The next usable ATG codon present in the correct frame is at nucleotide no. 177, and in this case, it is thought that at least two transmembrane regions will be deleted. The two systemic carnitine deficiency patients in this family were found to contain this mutated OCTN2 gene in both alleles. On the other hand, the parents and the two brothers of the patient, who have not developed the disease, carry the mutation on just one allele.

Figure 6:
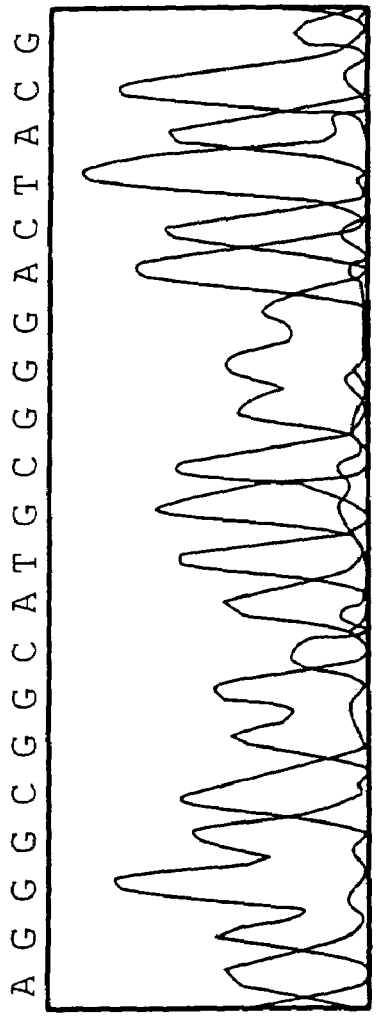
FIG. 6 shows the results of sequencing exon 1 of the OCTN2 gene. Compared to the normal OCTN2 gene (upper panel; wild-type; nucleotides 214 to 234 of SEQ ID NO:5), the OCTN2 of systemic carnitine deficiency patients (lower panel: SEQ ID NO:29) belonging to the AK family, show an insertion of a cytosine residue at the position indicated by the arrow.
Figure 6:
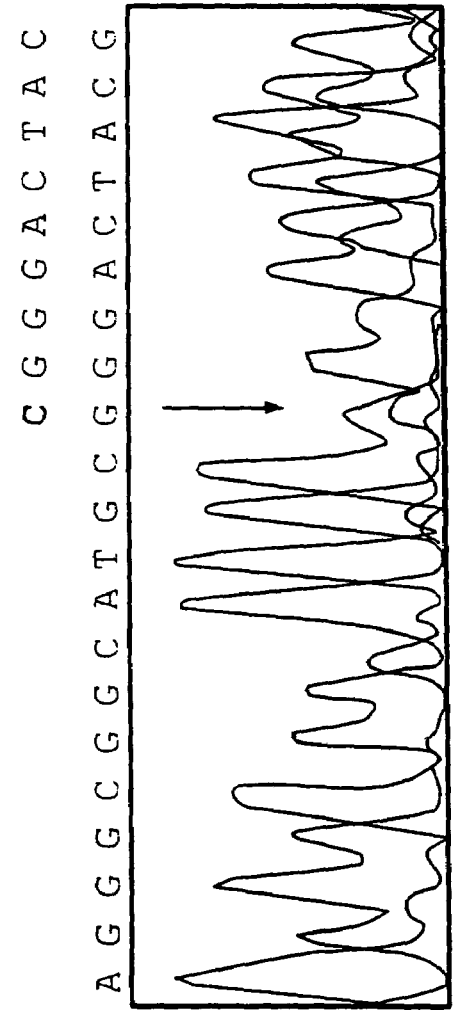
Figure 7:
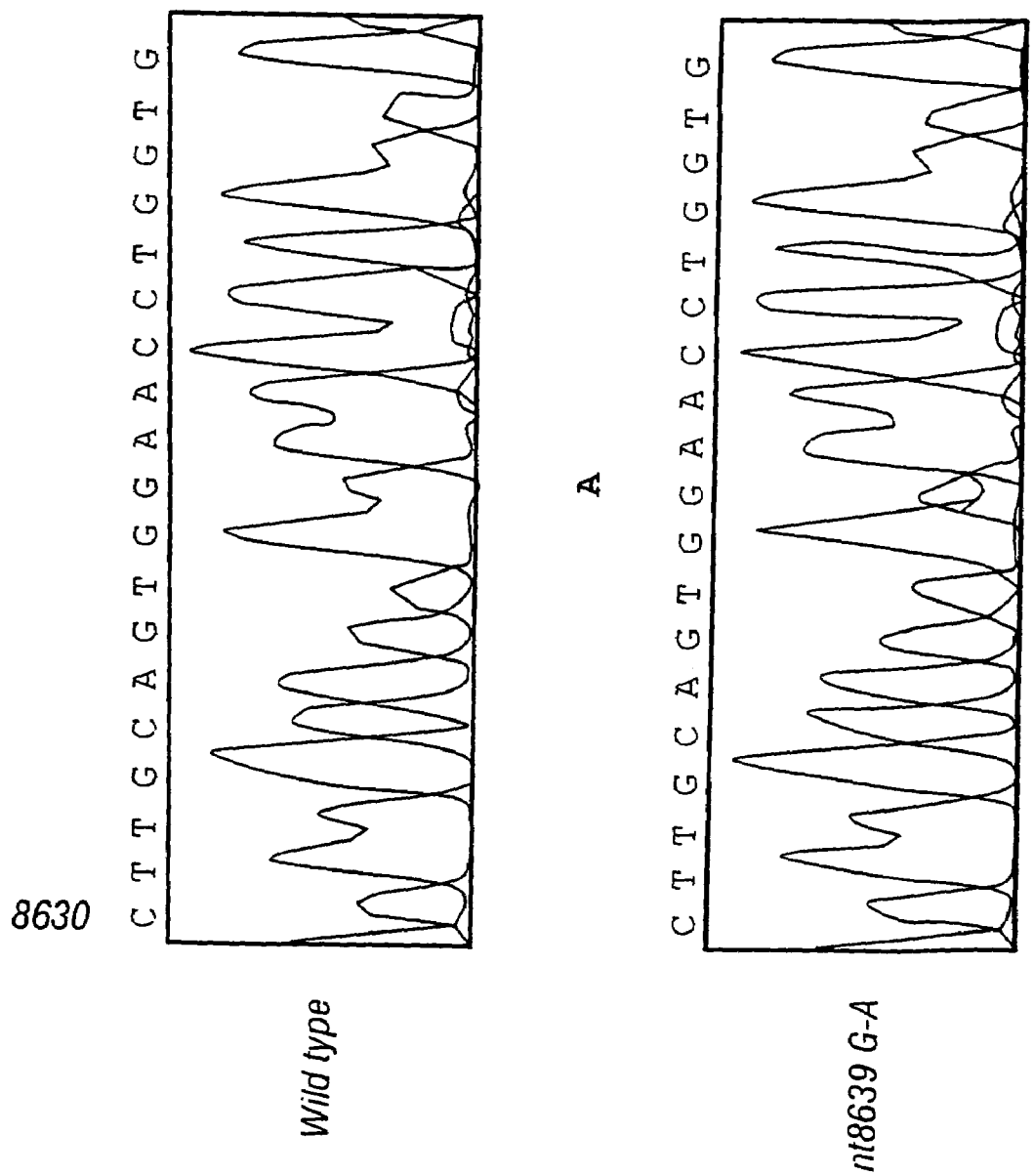
FIG. 7 shows the results of sequencing exon 2 of the OCTN2 gene. Compared to the normal QCTN2 gene (upper panel; wild-type; nucleotides 8,630 to 8,648 of SEQ ID NO:5), the OCTN2 of systemic carnitine deficiency patients (lower panel; SEQ ID NO:30) belonging to the AK family, show a single nucleotide substitution (A has substituted G) as indicated by the arrow.
Figure 8:
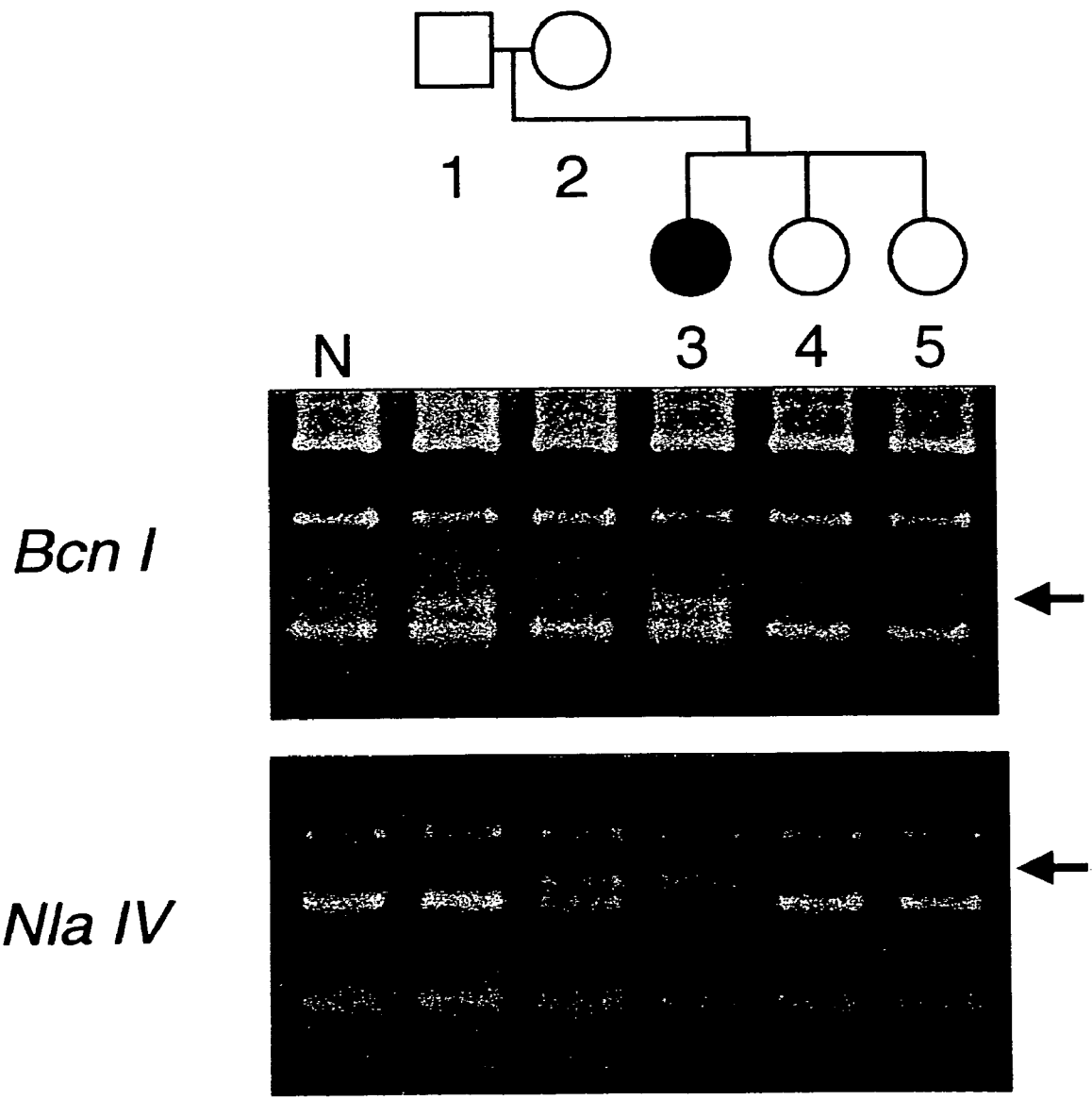
FIG. 8 is electrophoretic images showing the results of the analysis of two-types of mutations seen in the OCTN2 gene of a systemic carnitine deficiency patient belonging to the AK family using a PCR-RFLP method utilizing BcnI and NlaIV, respectively. The pedigree chart of this family is shown on top. Square indicates a male, circles females, and the filled circle indicates a systemic carnitine deficiency patient. "N" shows the results of the normal gene used as the control. The fragments shown by the arrows derived from the mutant gene.

In the second family (AK family), the systemic carnitine patients were found to contain two types of mutated OCTN2 genes. One mutation was a cytosine insertion just after the initiation codon, which is thought to cause a frame shift and prevent the proper protein from being produced (FIG. 6). The other mutation is a single base substitution (G to A) in the codon encoding the 132$^{nd}$ tryptophan (TGG). This mutation had altered the codon into a stop codon (TGA) (FIG. 7). These mutations are thought to prevent the production of active OCTN2 proteins in patients. These mutations can be detected by PCR-RFLP analysis using BcnI, NlaIV restriction enzymes, respectively, which revealed that the patient's parents who have not developed the disease, had one of each of the mutations, and the patient's sisters who have not developed the disease, do not have any mutated genes (FIG. 8).

Figure 9:
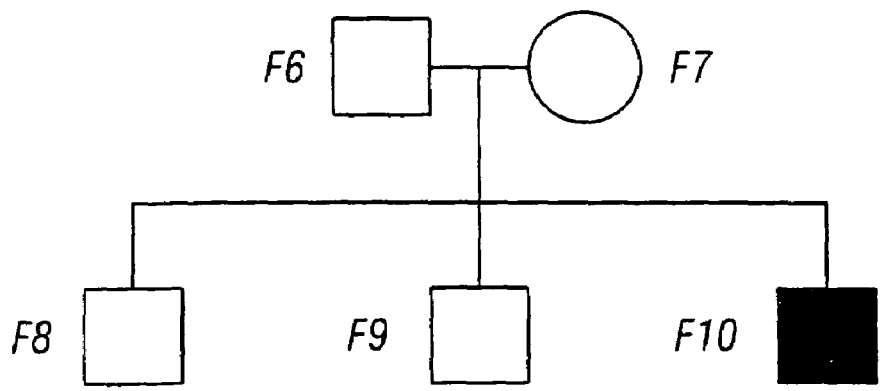
FIG. 9 shows the results of the sequencing analysis of the intron 8/exon 9 of the OCTN2 gene. Compared to the normal gene (normal; nucleotides 23,925 to 23,943 of SEQ ID NO:5), the gene deriving from the patient belonging to the TH family (patient; SEQ ID NO:31) has a splicing site mutation (AG to AA) in the 3' end of intron 8. The pedigree chart of this family is shown on top. Squares indicate males, the circle a female, and filled square indicates a systemic carnitine deficiency patient.
Figure 9:
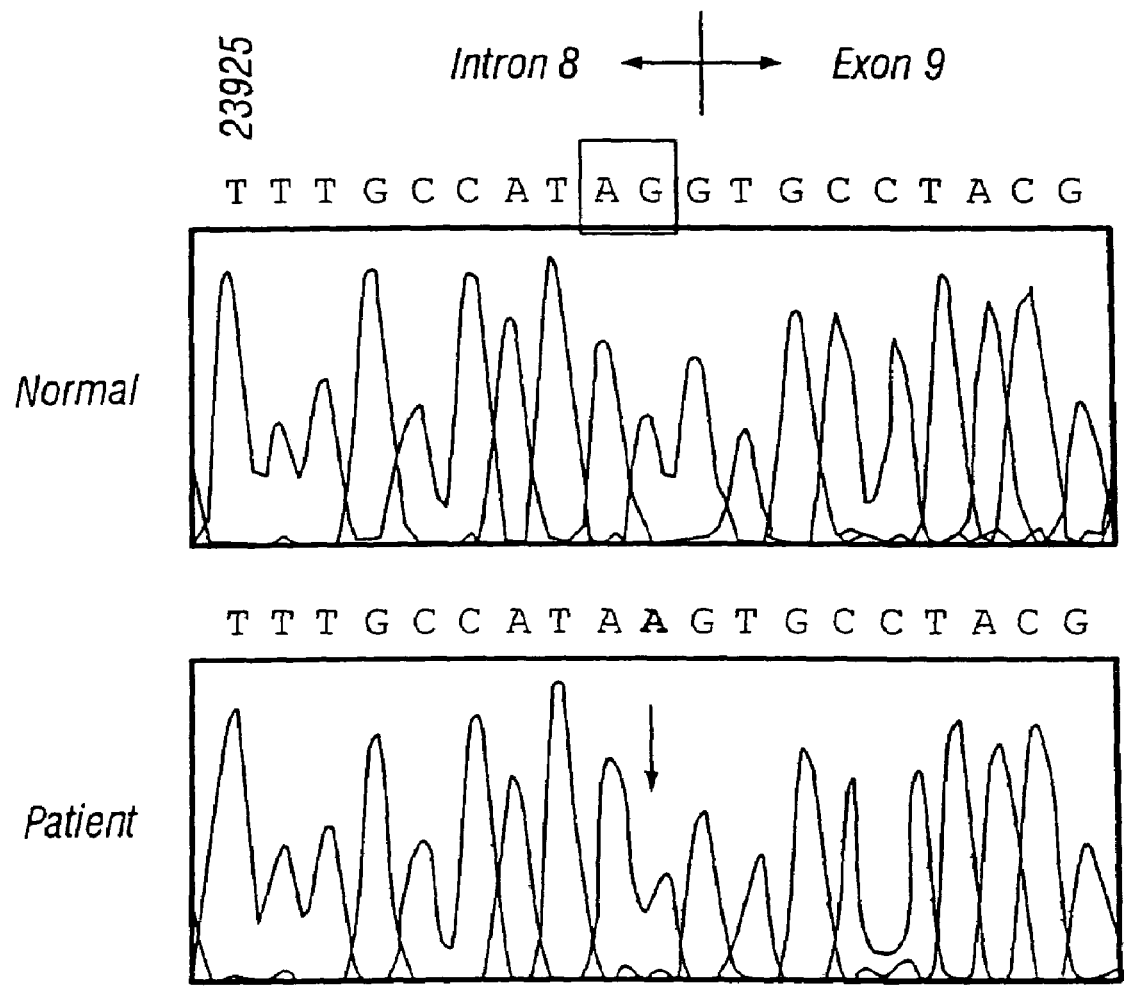

In the third family (TH family), a mutation (AG to AA) was found in the splicing site in the 3' end of the intron eight of the OCTN2 gene (FIG. 9). This mutation prevents the gene from undergoing normal splicing, and thus, it is expected that the normal protein would not be produced. Sequencing analysis showed that the systemic carnitine deficiency patient belonging to this family had this mutation in both alleles. On the other hand, the patient's parents and one of the brothers who have not developed the disease had one mutated allele.

The above results revealed that systemic carnitine deficiency is a genetic disease caused by mutations in the OCTN2 gene. Thus, the present invention enables definitive diagnosis, prenatal diagnosis and such, of systemic carnitine deficiency by examining mutations in the OCTN2 gene using analyses described herein, as well as other methods. The present invention also enables treatment of systemic carnitine deficiency by treatments such as gene therapy using the OCTN2 gene.

INDUSTRIAL APPLICABILITY

The present invention revealed that the OCTN2 gene is the gene responsible for systemic carnitine deficiency, thus enabling tests for the disease by detecting mutations in the OCTN2 gene and its protein. Moreover, the present invention facilitates treatment of systemic carnitine deficiency by utilizing the OCTN2 gene and its protein.

What is claimed is:

1. A method of testing whether an individual's genome carries a mutant OCTN2 allele that, in the homozygous state, may result in systemic carnitine deficiency, the method comprising
    (a) identifying an individual suspected of carrying the mutant allele; and
    (b) analyzing a nucleic acid sample from the individual to determine the presence or absence of a mutation in (i) DNA encoding OCTN2 (SEQ ID NO:1) or (ii) OCTN2 genomic DNA (SEQ ID NO:5) or (iii) a sequence that regulates expression of SEQ ID NO:5, wherein the presence of the mutation in (i) or (ii) or (iii) indicates that the individual carries a mutant OCTN2 allele that, in the homozygous state, may result in systemic carnitine deficiency.

2. A method of testing for, a mutation in an OCTN2 allele, the method comprising:
    (a) providing a DNA sample from an individual;
    (b) providing a pair of amplification primers, each primer comprising at least 15 nucleotides, wherein the pair of primers amplifies at least a part of DNA encoding SEQ ID NO:1, SEQ ID NO:5 or a sequence that regulates expression of SEQ ID NO:5;
    (c) subjecting the sample to amplification with the pair of primers, thereby generating amplified DNA; and
    (d) analyzing the amplified DNA to determine whether or not the DNA sample comprises a mutation in an OCTN2 allele.

3. The method of claim 2, wherein step (d) comprises subjecting the amplified DNA to restriction fragment length polymorphism analysis.

4. The method of claim 2, wherein step (d) comprises subjecting the amplified DNA to PCR-single-strand conformation polymorphism (PCR-SSCP) analysis.

5. The method of claim 2, wherein step (d) comprises:
    subjecting the amplified DNA, and similarly amplified DNA from a healthy control to denaturant gradient gel electrophoresis (DGGE), and
    comparing the mobility of the individual's amplified DNA to the mobility of the control amplified DNA, where a difference in mobility indicates the presence of a mutation in an OCTN2 allele of the individual.

6. The method of claim 2, wherein the pair of primers is:

OCN2 43
(5'-GCAGGACCAAGGCGGCGGTGTCAG-3', SEQ ID NO:6) and

OCN2 44
(5'-AGACTAGAGGAAAAACGGGATAGC-3', SEQ ID NO:7);

OCN2 25
(5'-AGATTTTTAGGAGCAAGCGTTAGA-3' SEQ ID NO:8) and

OCN2 26
(5'-GAGGCAGACACCGTGGCACTACTA-3', SEQ ID NO:9);

OCN2 27
(5'-TTCACACCCACTTACTGGATGGAT-3' SEQ ID NO:10) and

OCN2 50
(5'-ATTCTGTTTTGTTTTGGCTCTTTT-3', SEQ ID NO:11);

OCN2 31
(5'-AGCAGGGCCTGGGCTGACATAGAC-3', SEQ ID NO:12) and

OCN2 32
(5'-AAAGGACCTGACTCCAAGATGATA-3', SEQ ID NO:13);

OCN2 33
(5'-TCTGACCACCTCTTCTTCCCATAC-3', SEQ ID NO:14) and

OCN2 34
(5'-GCCTCCTCAGCCACTGTCGGTAAC-3', SEQ ID NO:15);

OCN2 35
(5'-ATGTTGTTCCTTTTGTTATCTTAT-3', SEQ ID NO:16) and

OCN2 36
(5'-CTTGTTTTCTTGTGTATCGTTATC-3', SEQ ID NO:17);

OCN2 37
(5'-TATGTTTGTTTTGCTCTCAATAGC-3', SEQ ID NO:18) and

OCN2 40
(5'-TCTGTGAGAGGGAGTTTGCGAGTA-3', SEQ ID NO:19);
or
OCN2 41
(5'-TACGACCGCTTCCTGCCCTACATT-3', SEQ ID NO:20) and

OCN2 42
(5'-TCATTCTGCTCCATCTTCATTACC-3', SEQ ID NO:21).

7. The method of claim 2, wherein the mutation comprises a deletion.

8. The method of claim 7, wherein the deletion comprises a deletion in exon 1.

9. The method of claim 8, wherein the deletion affects the initiation codon.

10. The method of claim 8, wherein the deletion comprises a deletion of 113 nucleotides.

11. The method of claim 2, wherein the mutation comprises an insertion.

12. The method of claim 11, wherein the insertion causes a frame shift.

13. The method of claim 11, wherein the insertion comprises an insertion of a cytidine residue in exon 1.

14. The method of claim 2, wherein the mutation comprises a nucleotide substitution.

15. The method of claim 14, wherein the substitution creates a stop codon.

16. The method of claim 14, wherein the substitution comprises a guanosine to adenosine substitution in the codon that encodes $Trp^{132}$.

17. The method of claim 2, wherein the mutation comprises a mutation in an intron splice site.

18. The method of claim 17, wherein the mutation prevents proper splicing from occurring.

19. The method of claim 17, wherein the splice site is located in intron 8.

20. The method of claim 19, wherein the mutation is a guanosine to adenosine substitution in the 3' end of intron 8.

21. The method of claim 2, wherein the individual of (a) is suspected of carrying a mutation correlated with systemic carnitine deficiency.

22. The method of claim 2, wherein the mutation, if present on both OCTN2 alleles, is correlated with systemic carnitine deficiency.

* * * * *

UNITED STATES PATENT AND TRADEMARK OFFICE
CERTIFICATE OF CORRECTION

PATENT NO. : 7,413,860 B2
APPLICATION NO. : 10/940500
DATED : August 19, 2008
INVENTOR(S) : Nezu et al.

Page 1 of 1

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 236 days Delete the phrase "by 236 days" and insert -- by 253 days --

Signed and Sealed this

Twentieth Day of January, 2009

JON W. DUDAS
*Director of the United States Patent and Trademark Office*

UNITED STATES PATENT AND TRADEMARK OFFICE
Certificate

Patent No. 7,413,860 B2                                                     Patented: August 19, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jun-Ihi Nezu, Ibaraki (JP); Asuka Ose, Ibaraki (JP); and Akira Tsuji, Ishikawa (JP).

Signed and Sealed this Twenty-seventh Day of October 2009.

ANDREW J. WANG
*Supervisory Patent Examiner*
Art Unit 1656

UNITED STATES PATENT AND TRADEMARK OFFICE
Certificate

Patent No. 7,413,860 B2                                                  Patented: August 19, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jun-Ichi Nezu, Ibaraki (JP); Asuka Ose, Ibaraki (JP); and Akira Tsuji, Ishikawa (JP).

Signed and Sealed this Fifteenth Day of December 2009.

Andrew J. Wang
                                                                                      *Supervisory Patent Examiner*
                                                                                                 Art Unit 1656

SEQUENCE LISTING

<160> NUMBER OF SEQ ID NOS: 31

<210> SEQ ID NO 1
<211> LENGTH: 557
<212> TYPE: PRT
<213> ORGANISM: Homo sapiens

<400> SEQUENCE: 1

```
Met Arg Asp Tyr Asp Glu Val Thr Ala Phe Leu Gly Glu Trp Gly Pro
 1               5                  10                  15

Phe Gln Arg Leu Ile Phe Phe Leu Leu Ser Ala Ser Ile Ile Pro Asn
            20                  25                  30

Gly Phe Thr Gly Leu Ser Ser Val Phe Leu Ile Ala Thr Pro Glu His
        35                  40                  45

Arg Cys Arg Val Pro Asp Ala Ala Asn Leu Ser Ser Ala Trp Arg Asn
    50                  55                  60

His Thr Val Pro Leu Arg Leu Arg Asp Gly Arg Glu Val Pro His Ser
65                  70                  75                  80

Cys Arg Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
            100                 105                 110

Cys Leu Asp Gly Trp Glu Phe Ser Gln Asp Val Tyr Leu Ser Thr Ile
        115                 120                 125

Val Thr Glu Trp Asn Leu Val Cys Glu Asp Asp Trp Lys Ala Pro Leu
    130                 135                 140

Thr Ile Ser Leu Phe Phe Val Gly Val Leu Leu Gly Ser Phe Ile Ser
145                 150                 155                 160

Gly Gln Leu Ser Asp Arg Phe Gly Arg Lys Asn Val Leu Phe Val Thr
                165                 170                 175

Met Gly Met Gln Thr Gly Phe Ser Phe Leu Gln Ile Phe Ser Lys Asn
            180                 185                 190

Phe Glu Met Phe Val Val Leu Phe Val Leu Val Gly Met Gly Gln Ile
        195                 200                 205

Ser Asn Tyr Val Ala Ala Phe Val Leu Gly Thr Glu Ile Leu Gly Lys
    210                 215                 220

Ser Val Arg Ile Ile Phe Ser Thr Leu Gly Val Cys Ile Phe Tyr Ala
225                 230                 235                 240

Phe Gly Tyr Met Val Leu Pro Leu Phe Ala Tyr Phe Ile Arg Asp Trp
                245                 250                 255

Arg Met Leu Leu Val Ala Leu Thr Met Pro Gly Val Leu Cys Val Ala
            260                 265                 270

Leu Trp Trp Phe Ile Pro Glu Ser Pro Arg Trp Leu Ile Ser Gln Gly
        275                 280                 285

Arg Phe Glu Glu Ala Glu Val Ile Ile Arg Lys Ala Ala Lys Ala Asn
```

```
                    290                 295                 300
Gly Ile Val Val Pro Ser Thr Ile Phe Asp Pro Ser Glu Leu Gln Asp
305                 310                 315                 320

Leu Ser Ser Lys Lys Gln Gln Ser His Asn Ile Leu Asp Leu Leu Arg
                325                 330                 335

Thr Trp Asn Ile Arg Met Val Thr Ile Met Ser Ile Met Leu Trp Met
            340                 345                 350

Thr Ile Ser Val Gly Tyr Phe Gly Leu Ser Leu Asp Thr Pro Asn Leu
        355                 360                 365

His Gly Asp Ile Phe Val Asn Cys Phe Leu Ser Ala Met Val Glu Val
370                 375                 380

Pro Ala Tyr Val Leu Ala Trp Leu Leu Leu Gln Tyr Leu Pro Arg Arg
385                 390                 395                 400

Tyr Ser Met Ala Thr Ala Leu Phe Leu Gly Gly Ser Val Leu Leu Phe
                405                 410                 415

Met Gln Leu Val Pro Pro Asp Leu Tyr Tyr Leu Ala Thr Val Leu Val
            420                 425                 430

Met Val Gly Lys Phe Gly Val Thr Ala Ala Phe Ser Met Val Tyr Val
        435                 440                 445

Tyr Thr Ala Glu Leu Tyr Pro Thr Val Val Arg Asn Met Gly Val Gly
    450                 455                 460

Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Leu Pro Glu Ser
            500                 505                 510

Phe Gly Thr Pro Leu Pro Asp Thr Ile Asp Gln Met Leu Arg Val Lys
        515                 520                 525

Gly Met Lys His Arg Lys Thr Pro Ser His Thr Arg Met Leu Lys Asp
    530                 535                 540

Gly Gln Glu Arg Pro Thr Ile Leu Lys Ser Thr Ala Phe
545                 550                 555

<210> SEQ ID NO 2
<211> LENGTH: 1831
<212> TYPE: DNA
<213> ORGANISM: Homo sapiens
<220> FEATURE:
<221> NAME/KEY: CDS
<222> LOCATION: (124)..(1794)

<400> SEQUENCE: 2
cggacggtct tgggtcgcct gctgcctggc ttgcctggtc ggcggcgggt gccccgcgcg      60
cacgcgcaaa gcccgccgcg ttcccagacc ccaggccgcg ctctgtgggc ctctgagggc     120 ggc atg cgg gac tac gac gag gtg acc gcc ttc ctg ggc gag tgg ggg       168
    Met Arg Asp Tyr Asp Glu Val Thr Ala Phe Leu Gly Glu Trp Gly
    1               5                   10                  15 ccc ttc cag cgc ctc atc ttc ttc ctg ctc agc gcc agc atc atc ccc       216
Pro Phe Gln Arg Leu Ile Phe Phe Leu Leu Ser Ala Ser Ile Ile Pro
                20                  25                  30 aat ggc ttc acc ggc ctg tcc tcc gtg ttc ctg ata gcg acc ccg gag       264
Asn Gly Phe Thr Gly Leu Ser Ser Val Phe Leu Ile Ala Thr Pro Glu
            35                  40                  45 cac cgc tgc cgg gtg ccg gac gcc gcg aac ctg agc agc gcc tgg cgc       312
His Arg Cys Arg Val Pro Asp Ala Ala Asn Leu Ser Ser Ala Trp Arg
```

-continued

```
              50                  55                  60
aac cac act gtc cca ctg cgg ctg cgg gac ggc cgc gag gtg ccc cac    360
Asn His Thr Val Pro Leu Arg Leu Arg Asp Gly Arg Glu Val Pro His
         65                  70                  75 agc tgc cgc cgc tac cgg ctc gcc acc atc gcc aac ttc tcg gcg ctc    408
Ser Cys Arg Arg Tyr Arg Leu Ala Thr Ile Ala Asn Phe Ser Ala Leu
 80                  85                  90                  95 ggg ctg gag ccg ggg cgc gac gtg gac ctg ggg cag ctg gag cag gag    456
Gly Leu Glu Pro Gly Arg Asp Val Asp Leu Gly Gln Leu Glu Gln Glu
                    100                 105                 110 agc tgt ctg gat ggc tgg gag ttc agt cag gac gtc tac ctg tcc acc    504
Ser Cys Leu Asp Gly Trp Glu Phe Ser Gln Asp Val Tyr Leu Ser Thr
            115                 120                 125 att gtg acc gag tgg aac ctg gtg tgt gag gac gac tgg aag gcc cca    552
Ile Val Thr Glu Trp Asn Leu Val Cys Glu Asp Asp Trp Lys Ala Pro
        130                 135                 140 ctc aca atc tcc ttg ttc ttc gtg ggt gtg ctg ttg ggc tcc ttc att    600
Leu Thr Ile Ser Leu Phe Phe Val Gly Val Leu Leu Gly Ser Phe Ile
    145                 150                 155 tca ggg cag ctg tca gac agg ttt ggc cgg aag aat gtg ctg ttc gtg    648
Ser Gly Gln Leu Ser Asp Arg Phe Gly Arg Lys Asn Val Leu Phe Val
160                 165                 170                 175 acc atg ggc atg cag aca ggc ttc agc ttc ctg cag atc ttc tcg aag    696
Thr Met Gly Met Gln Thr Gly Phe Ser Phe Leu Gln Ile Phe Ser Lys
                180                 185                 190 aat ttt gag atg ttt gtc gtg ctg ttt gtc ctt gta ggc atg ggc cag    744
Asn Phe Glu Met Phe Val Val Leu Phe Val Leu Val Gly Met Gly Gln
            195                 200                 205 atc tcc aac tat gtg gca gca ttt gtc ctg ggg aca gaa att ctt ggc    792
Ile Ser Asn Tyr Val Ala Ala Phe Val Leu Gly Thr Glu Ile Leu Gly
        210                 215                 220 aag tca gtt cgt ata ata ttc tct acg tta gga gtg tgc ata ttt tat    840
Lys Ser Val Arg Ile Ile Phe Ser Thr Leu Gly Val Cys Ile Phe Tyr
    225                 230                 235 gca ttt ggc tac atg gtg ctg cca ctg ttt gct tac ttc atc cga gac    888
Ala Phe Gly Tyr Met Val Leu Pro Leu Phe Ala Tyr Phe Ile Arg Asp
240                 245                 250                 255 tgg cgg atg ctg ctg gtg gcg ctg acg atg ccg ggg gtg ctg tgc gtg    936
Trp Arg Met Leu Leu Val Ala Leu Thr Met Pro Gly Val Leu Cys Val
                260                 265                 270 gca ctc tgg tgg ttc atc cct gag tcc ccc cga tgg ctc atc tct cag    984
Ala Leu Trp Trp Phe Ile Pro Glu Ser Pro Arg Trp Leu Ile Ser Gln
            275                 280                 285 gga cga ttt gaa gag gca gag gtg atc atc cgc aag gct gcc aaa gcc   1032
Gly Arg Phe Glu Glu Ala Glu Val Ile Ile Arg Lys Ala Ala Lys Ala
        290                 295                 300 aat ggg att gtt gtg cct tcc act atc ttt gac ccg agt gag tta caa   1080
Asn Gly Ile Val Val Pro Ser Thr Ile Phe Asp Pro Ser Glu Leu Gln
305                 310                 315 gac cta agt tcc aag aag cag cag tcc cac aac att ctg gat ctg ctt   1128
Asp Leu Ser Ser Lys Lys Gln Gln Ser His Asn Ile Leu Asp Leu Leu
320                 325                 330                 335 cga acc tgg aat atc cgg atg gtc acc atc atg tcc ata atg ctg tgg   1176
Arg Thr Trp Asn Ile Arg Met Val Thr Ile Met Ser Ile Met Leu Trp
                340                 345                 350 atg acc ata tca gtg ggc tat ttt ggg ctt tcg ctt gat act cct aac   1224
Met Thr Ile Ser Val Gly Tyr Phe Gly Leu Ser Leu Asp Thr Pro Asn
            355                 360                 365 ttg cat ggg gac atc ttt gtg aac tgc ttc ctt tca gcg atg gtt gaa   1272
```

| | | | | | | | | | | | | | | | |
|---|---|---|---|---|---|---|---|---|---|---|---|---|---|---|---|
|Leu|His|Gly|Asp|Ile|Phe|Val|Asn|Cys|Phe|Leu|Ser|Ala|Met|Val|Glu|
| | |370| | | |375| | | |380| | | | | |

```
gtc cca gca tat gtg ttg gcc tgg ctg ctg ctg caa tat ttg ccc cgg    1320
Val Pro Ala Tyr Val Leu Ala Trp Leu Leu Leu Gln Tyr Leu Pro Arg
    385                 390                 395 cgc tat tcc atg gcc act gcc ctc ttc ctg ggt ggc agt gtc ctt ctc    1368
Arg Tyr Ser Met Ala Thr Ala Leu Phe Leu Gly Gly Ser Val Leu Leu
400                 405                 410                 415 ttc atg cag ctg gta ccc cca gac ttg tat tat ttg gct aca gtc ctg    1416
Phe Met Gln Leu Val Pro Pro Asp Leu Tyr Tyr Leu Ala Thr Val Leu
                420                 425                 430 gtg atg gtg ggc aag ttt gga gtc acg gct gcc ttt tcc atg gtc tac    1464
Val Met Val Gly Lys Phe Gly Val Thr Ala Ala Phe Ser Met Val Tyr
            435                 440                 445 gtg tac aca gcc gag ctg tat ccc aca gtg gtg aga aac atg ggt gtg    1512
Val Tyr Thr Ala Glu Leu Tyr Pro Thr Val Val Arg Asn Met Gly Val
        450                 455                 460 gga gtc agc tcc aca gca tcc cgc ctg ggc agc atc ctg tct ccc tac    1560
Gly Val Ser Ser Thr Ala Ser Arg Leu Gly Ser Ile Leu Ser Pro Tyr
    465                 470                 475 ttc gtt tac ctt ggt gcc tac gac cgc ttc ctg ccc tac att ctc atg    1608
Phe Val Tyr Leu Gly Ala Tyr Asp Arg Phe Leu Pro Tyr Ile Leu Met
480                 485                 490                 495 gga agt ctg acc atc ctg aca gcc atc ctc acc ttg ttt ctc cca gag    1656
Gly Ser Leu Thr Ile Leu Thr Ala Ile Leu Thr Leu Phe Leu Pro Glu
                500                 505                 510 agc ttc ggt acc cca ctc cca gac acc att gac cag atg cta aga gtc    1704
Ser Phe Gly Thr Pro Leu Pro Asp Thr Ile Asp Gln Met Leu Arg Val
            515                 520                 525 aaa gga atg aaa cac aga aaa act cca agt cac aca agg atg tta aaa    1752
Lys Gly Met Lys His Arg Lys Thr Pro Ser His Thr Arg Met Leu Lys
        530                 535                 540 gat ggt caa gaa agg ccc aca atc ctt aaa agc aca gcc ttc            1794
Asp Gly Gln Glu Arg Pro Thr Ile Leu Lys Ser Thr Ala Phe
    545                 550                 555 taacatcgct tccagtaagg gagaaactga agaggaa                           1831

<210> SEQ ID NO 3
<211> LENGTH: 557
<212> TYPE: PRT
<213> ORGANISM: Mus musculus

<400> SEQUENCE: 3

Met Arg Asp Tyr Asp Glu Val Thr Ala Phe Leu Gly Glu Trp Gly Pro
1               5                   10                  15

Phe Gln Arg Leu Ile Phe Phe Leu Leu Ser Ala Ser Ile Ile Pro Asn
                20                  25                  30

Gly Phe Asn Gly Met Ser Ile Val Phe Leu Ala Gly Thr Pro Glu His
            35                  40                  45

Arg Cys Leu Val Pro His Thr Val Asn Leu Ser Ser Ala Trp Arg Asn
        50                  55                  60

His Ser Ile Pro Leu Glu Thr Lys Asp Gly Arg Gln Val Pro Gln Lys
65                  70                  75                  80

Cys Arg Arg Tyr Arg Leu Ala Thr Ile Ala Asn Phe Ser Glu Leu Gly
                85                  90                  95

Leu Glu Pro Gly Arg Asp Val Asp Leu Glu Gln Leu Glu Gln Glu Ser
            100                 105                 110

Cys Leu Asp Gly Trp Glu Tyr Asp Lys Asp Val Phe Leu Ser Thr Ile
```

-continued

```
            115                 120                 125
Val Thr Glu Trp Asp Leu Val Cys Lys Asp Asp Trp Lys Ala Pro Leu
130                 135                 140

Thr Thr Ser Leu Phe Phe Val Gly Val Leu Met Gly Ser Phe Ile Ser
145                 150                 155                 160

Gly Gln Leu Ser Asp Arg Phe Gly Arg Lys Asn Val Leu Phe Leu Thr
                165                 170                 175

Met Gly Met Gln Thr Gly Phe Ser Phe Leu Gln Val Phe Ser Val Asn
            180                 185                 190

Phe Glu Met Phe Thr Val Leu Phe Val Leu Val Gly Met Gly Gln Ile
        195                 200                 205

Ser Asn Tyr Val Ala Ala Phe Val Leu Gly Thr Glu Ile Leu Ser Lys
210                 215                 220

Ser Ile Arg Ile Ile Phe Ala Thr Leu Gly Val Cys Ile Phe Tyr Ala
225                 230                 235                 240

Phe Gly Phe Met Val Leu Pro Leu Phe Ala Tyr Phe Ile Arg Asp Trp
                245                 250                 255

Arg Met Leu Leu Leu Ala Leu Thr Val Pro Gly Val Leu Cys Gly Ala
            260                 265                 270

Leu Trp Trp Phe Ile Pro Glu Ser Pro Arg Trp Leu Ile Ser Gln Gly
        275                 280                 285

Arg Ile Lys Glu Ala Glu Val Ile Ile Arg Lys Ala Ala Lys Ile Asn
    290                 295                 300

Gly Ile Val Ala Pro Ser Thr Ile Phe Asp Pro Ser Glu Leu Gln Asp
305                 310                 315                 320

Leu Asn Ser Thr Lys Pro Gln Leu His His Ile Tyr Asp Leu Ile Arg
                325                 330                 335

Thr Arg Asn Ile Arg Val Ile Thr Ile Met Ser Ile Ile Leu Trp Leu
            340                 345                 350

Thr Ile Ser Val Gly Tyr Phe Gly Leu Ser Leu Asp Thr Pro Asn Leu
        355                 360                 365

His Gly Asp Ile Tyr Val Asn Cys Phe Leu Leu Ala Ala Val Glu Val
    370                 375                 380

Pro Ala Tyr Val Leu Ala Trp Leu Leu Leu Gln Tyr Leu Pro Arg Arg
385                 390                 395                 400

Tyr Ser Ile Ser Ala Ala Leu Phe Leu Gly Gly Ser Val Leu Leu Phe
                405                 410                 415

Met Gln Leu Val Pro Ser Glu Leu Phe Tyr Leu Ser Thr Ala Leu Val
            420                 425                 430

Met Val Gly Lys Phe Gly Ile Thr Ser Ala Tyr Ser Met Val Tyr Val
        435                 440                 445

Tyr Thr Ala Glu Leu Tyr Pro Thr Val Val Arg Asn Met Gly Val Gly
    450                 455                 460

Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Phe Pro Glu Ser
            500                 505                 510

Phe Gly Val Pro Leu Pro Asp Thr Ile Asp Gln Met Leu Arg Val Lys
        515                 520                 525

Gly Ile Lys Gln Trp Gln Ile Gln Ser Gln Thr Arg Met Gln Lys Asp
    530                 535                 540
```

```
Gly Glu Glu Ser Pro Thr Val Leu Lys Ser Thr Ala Phe
545                 550                 555

<210> SEQ ID NO 4
<211> LENGTH: 1888
<212> TYPE: DNA
<213> ORGANISM: Mus musculus
<220> FEATURE:
<221> NAME/KEY: CDS
<222> LOCATION: (60)..(1730)

<400> SEQUENCE: 4
ctcccgcgcc acggtgtccc cttattccca tacgggcgct gtgggaggct gaggacggc       59 atg cgg gac tac gac gag gtg acc gcc ttc cta ggc gag tgg ggg ccc      107
Met Arg Asp Tyr Asp Glu Val Thr Ala Phe Leu Gly Glu Trp Gly Pro
 1               5                  10                  15 ttc cag cgc ctc atc ttc ttc ctg ctc agc gcc agc atc atc ccc aat      155
Phe Gln Arg Leu Ile Phe Phe Leu Leu Ser Ala Ser Ile Ile Pro Asn
             20                  25                  30 ggc ttc aat ggt atg tcc atc gtg ttc ctg gcg ggg acc ccg gag cac      203
Gly Phe Asn Gly Met Ser Ile Val Phe Leu Ala Gly Thr Pro Glu His
         35                  40                  45 cgt tgc ctt gtg cct cac acc gtg aac ctg agc agc gcg tgg cgc aac      251
Arg Cys Leu Val Pro His Thr Val Asn Leu Ser Ser Ala Trp Arg Asn
     50                  55                  60 cac agt atc ccg ttg gag acg aag gac gga cga cag gtg cct cag aaa      299
His Ser Ile Pro Leu Glu Thr Lys Asp Gly Arg Gln Val Pro Gln Lys
 65                  70                  75                  80 tgc cgc cgc tac cga ctg gcc acc atc gcc aac ttc tct gag cta ggg      347
Cys Arg Arg Tyr Arg Leu Ala Thr Ile Ala Asn Phe Ser Glu Leu Gly
                 85                  90                  95 ctg gag ccg ggg cgg gac gtg gac ctg gag cag ctg gag cag gag agc      395
Leu Glu Pro Gly Arg Asp Val Asp Leu Glu Gln Leu Glu Gln Glu Ser
            100                 105                 110 tgc ctg gat ggc tgg gag tac gac aag gac gtc ttc ctg tcc acc atc      443
Cys Leu Asp Gly Trp Glu Tyr Asp Lys Asp Val Phe Leu Ser Thr Ile
        115                 120                 125 gtg aca gag tgg gac ctg gtg tgt aag gat gac tgg aaa gcc cca ctc      491
Val Thr Glu Trp Asp Leu Val Cys Lys Asp Asp Trp Lys Ala Pro Leu
    130                 135                 140 acc acc tcc ttg ttt ttc gtg ggt gtg ctg atg ggc tcc ttc att tca      539
Thr Thr Ser Leu Phe Phe Val Gly Val Leu Met Gly Ser Phe Ile Ser
145                 150                 155                 160 gga cag ctc tca gac agg ttt ggt cgc aag aat gtg ctg ttt ttg acc      587
Gly Gln Leu Ser Asp Arg Phe Gly Arg Lys Asn Val Leu Phe Leu Thr
                165                 170                 175 atg ggc atg cag act ggc ttc agc ttc ctg cag gtc ttc tct gtg aac      635
Met Gly Met Gln Thr Gly Phe Ser Phe Leu Gln Val Phe Ser Val Asn
            180                 185                 190 ttc gag atg ttt aca gtg ctt ttt gtc ctt gtt ggc atg ggt cag atc      683
Phe Glu Met Phe Thr Val Leu Phe Val Leu Val Gly Met Gly Gln Ile
        195                 200                 205 tcc aac tac gtg gca gca ttt gtc ctg gga aca gaa att ctt tcc aag      731
Ser Asn Tyr Val Ala Ala Phe Val Leu Gly Thr Glu Ile Leu Ser Lys
    210                 215                 220 tca att cga att ata ttc gcc acc tta gga gtt tgc ata ttt tat gcg      779
Ser Ile Arg Ile Ile Phe Ala Thr Leu Gly Val Cys Ile Phe Tyr Ala
225                 230                 235                 240 ttt ggc ttc atg gtg ctg cca ctg ttt gca tac ttc atc aga gac tgg      827
Phe Gly Phe Met Val Leu Pro Leu Phe Ala Tyr Phe Ile Arg Asp Trp
```

```
                -continued
        245             250             255
agg atg ctg ctg ctg gcg ctc act gtg cca ggg gtg cta tgt ggg gct     875
Arg Met Leu Leu Leu Ala Leu Thr Val Pro Gly Val Leu Cys Gly Ala
            260             265             270 ctc tgg tgg ttc atc cct gag tcc cca cga tgg ctc atc tct caa ggc     923
Leu Trp Trp Phe Ile Pro Glu Ser Pro Arg Trp Leu Ile Ser Gln Gly
        275             280             285 cga att aaa gag gca gag gtg atc atc cgc aaa gct gcc aaa atc aat     971
Arg Ile Lys Glu Ala Glu Val Ile Ile Arg Lys Ala Ala Lys Ile Asn
    290             295             300 ggg att gtt gca cct tcc act atc ttc gat cca agt gag tta caa gac    1019
Gly Ile Val Ala Pro Ser Thr Ile Phe Asp Pro Ser Glu Leu Gln Asp
305             310             315             320 tta aat tct acg aag cct cag ttg cac cac att tat gat ctg atc cga    1067
Leu Asn Ser Thr Lys Pro Gln Leu His His Ile Tyr Asp Leu Ile Arg
            325             330             335 aca cgg aat atc agg gtc atc acc atc atg tct ata atc ctg tgg ctg    1115
Thr Arg Asn Ile Arg Val Ile Thr Ile Met Ser Ile Ile Leu Trp Leu
        340             345             350 acc ata tca gtg ggc tat ttt gga cta tct ctt gac act cct aac ttg    1163
Thr Ile Ser Val Gly Tyr Phe Gly Leu Ser Leu Asp Thr Pro Asn Leu
    355             360             365 cat ggg gac atc tat gtg aac tgc ttc cta ctg gcg gct gtt gaa gtc    1211
His Gly Asp Ile Tyr Val Asn Cys Phe Leu Leu Ala Ala Val Glu Val
370             375             380 cca gcc tat gtg ctg gcc tgg ctg ttg cag tac ttg ccc cgg cga        1259
Pro Ala Tyr Val Leu Ala Trp Leu Leu Gln Tyr Leu Pro Arg Arg
385             390             395             400 tat tct atc tcg gct gcc ctt ttc ctg ggt ggc agt gtc ctt ctc ttc    1307
Tyr Ser Ile Ser Ala Ala Leu Phe Leu Gly Gly Ser Val Leu Leu Phe
            405             410             415 atg cag ctg gtg cct tca gaa ttg ttt tac ttg tcc act gcc ctg gtg    1355
Met Gln Leu Val Pro Ser Glu Leu Phe Tyr Leu Ser Thr Ala Leu Val
        420             425             430 atg gtg ggg aag ttt gga atc acc tct gcc tac tcc atg gtc tat gtg    1403
Met Val Gly Lys Phe Gly Ile Thr Ser Ala Tyr Ser Met Val Tyr Val
    435             440             445 tac aca gct gag ctg tac ccc act gtg gtc aga aac atg ggt gtg ggg    1451
Tyr Thr Ala Glu Leu Tyr Pro Thr Val Val Arg Asn Met Gly Val Gly
450             455             460 gtc agc tcc aca gca tcc cgc ctt ggc agc atc ctg tct ccc tac ttt    1499
Val Ser Ser Thr Ala Ser Arg Leu Gly Ser Ile Leu Ser Pro Tyr Phe
465             470             475             480 gtt tac cta ggt gcc tat gat cgc ttc ctg cct tat att ctc atg gga    1547
Val Tyr Leu Gly Ala Tyr Asp Arg Phe Leu Pro Tyr Ile Leu Met Gly
            485             490             495 agt ctg acc atc ctg aca gct atc ctc acc ttg ttc ttc cct gag agc    1595
Ser Leu Thr Ile Leu Thr Ala Ile Leu Thr Leu Phe Phe Pro Glu Ser
        500             505             510 ttt ggt gtc cct ctc cca gat acc att gac cag atg cta agg gtc aaa    1643
Phe Gly Val Pro Leu Pro Asp Thr Ile Asp Gln Met Leu Arg Val Lys
    515             520             525 gga ata aaa cag tgg caa atc caa agc cag aca aga atg caa aaa gat    1691
Gly Ile Lys Gln Trp Gln Ile Gln Ser Gln Thr Arg Met Gln Lys Asp
530             535             540 ggt gaa gaa agc cca aca gtc cta aag agc aca gcc ttc taacaccctg    1740
Gly Glu Glu Ser Pro Thr Val Leu Lys Ser Thr Ala Phe
545             550             555 tccagaaggc aaaaaactga ttggaaacct tcatgttgtc agaaatgctc tccatgactg    1800
```

```
agggcttttc tgttctgtta accttgtgtc taacatgctc atggattggg gcatctgtcc      1860
tggagagtca ccttcctcta gggacacc                                        1888
```

<210> SEQ ID NO 5
<211> LENGTH: 25871
<212> TYPE: DNA
<213> ORGANISM: Homo sapiens
<220> FEATURE:
<221> NAME/KEY: exon
<222> LOCATION: (1)..(614)
<220> FEATURE:
<221> NAME/KEY: intron
<222> LOCATION: (615)..(8636)
<220> FEATURE:
<221> NAME/KEY: exon
<222> LOCATION: (8637)..(8740)
<220> FEATURE:
<221> NAME/KEY: intron
<222> LOCATION: (8741)..(14409)
<220> FEATURE:
<221> NAME/KEY: exon
<222> LOCATION: (14410)..(14564)
<220> FEATURE:
<221> NAME/KEY: intron
<222> LOCATION: (14565)..(15590)
<220> FEATURE:
<221> NAME/KEY: exon
<222> LOCATION: (15591)..(15762)
<220> FEATURE:
<221> NAME/KEY: intron
<222> LOCATION: (15763)..(17282)
<220> FEATURE:
<221> NAME/KEY: exon
<222> LOCATION: (17283)..(17409)
<220> FEATURE:
<221> NAME/KEY: intron
<222> LOCATION: (17410)..(19178)
<220> FEATURE:
<221> NAME/KEY: exon
<222> LOCATION: (19179)..(19279)
<220> FEATURE:
<221> NAME/KEY: intron
<222> LOCATION: (19280)..(20947)
<220> FEATURE:
<221> NAME/KEY: exon
<222> LOCATION: (20948)..(21162)
<220> FEATURE:
<221> NAME/KEY: intron
<222> LOCATION: (21163)..(22690)
<220> FEATURE:
<221> NAME/KEY: exon
<222> LOCATION: (22691)..(22873)
<220> FEATURE:
<221> NAME/KEY: intron
<222> LOCATION: (22874)..(23934)
<220> FEATURE:
<221> NAME/KEY: exon
<222> LOCATION: (23935)..(24070)
<220> FEATURE:
<221> NAME/KEY: intron
<222> LOCATION: (24071)..(24443)
<220> FEATURE:
<221> NAME/KEY: exon
<222> LOCATION: (24444)..(25871)

<400> SEQUENCE: 5

```
gcggcccagg cccggaacct tccctggtcg tgcgccatat gtaaggccag ccgcggcagg       60
accaaggcgg cggtgtcagc tcgcgagcct acctccgcg dacggtcttg ggtcgcctgc      120
tgcctggctt gcctggtcgg cggcgggtgc cccgcgcgca cgcgcaaagc ccgccgcgtt      180
cccagacccc aggccgcgct ctgtgggcct ctgagggcgg catgcgggac tacgacgagg      240
tgaccgcctt cctgggcgag tgggggccct tccagcgcct catcttcttc ctgctcagcg      300
```

```
ccagcatcat ccccaatggc ttcaccggcc tgtcctccgt gttcctgata gcgaccccgg    360
agcaccgctg ccgggtgccg gacgccgcga acctgagcag cgcctggcgc aaccacactg    420
tcccactgcg gctgcgggac ggccgcgagg tgccccacag ctgccgccgc taccggctcg    480
ccaccatcgc caacttctcg gcgctcgggc tggagccggg gcgcgacgtg gacctggggc    540
agctggagca ggagagctgt ctggatggct gggagttcag tcaggacgtc tacctgtcca    600
ccattgtgac cgaggtgggt gccggcccct gctggggctg agaccagggc tcggaggacc    660
tgtcgcggtc cttgaacccg agctcctctc tcccagatgc gcactggacg ctgtcactcc    720
ccctccccca acggtcaaca ccctagcgat ggagaccctc cagccaggtg gcttgggaac    780
gcttcacgag gtgacctcca gccacagtgt gctcctccct gcacaggtgg tcagtctggc    840
ctcccgtcct gatggccact ttgaagaggg taccaggaag gtcctggcgg tccctgggcg    900
atgctctatg gccctgtgtg tccaggactt actctagttg gggttggggg tggtaagtag    960
cagagccagg acttgggcca ggggctatcc cgttttttcct ctagtctctt gatttctttt   1020
tagaagagaa gaaatacttc tctttcctga acttttaaaa gttaaataaa gcatgtgtat   1080
acaactgcct cttcccttt tcctctagtt actccttccc ctaccgtcca aacccaaaa     1140
acgacaatct ggtcatgccc tgtaagtaat tgtttgcctt ttcccatggt cagttgtcag   1200
tcttttttt ttttttttt tttgagaca gagtctcccct ctgtcaccag ctggagcgc      1260
agtcgtgtgt tcttggctca ctgcaacctt cgcagtcgtg cgttcttggc tcactgcaat   1320
cttcgccttc cgggctcaag tgattctcct gcctcagcct ccgagtagct gtgagccacg   1380
acgcccagct aattttttgtg tttttagtag agacggggtt tcaccgtgtt ggccaggatg   1440
gtctcgatct cttgacctcg tgatctgcct gcttctgcct gcaaagctgg gattacaacc   1500
gtgagccacc acgccaggcc gtcagttgtc actctttaag atccattcat ctgaagatgg   1560
gttcagggtg acttgttgac ctggaatatt ttctcaggta ttatgaggca aggctgtcgg   1620
ccagatttag ttaaagcata cagccttagg tcataggtg tgggggagcc tttctcattt    1680
ctcatcccct tggattttcc ctctgggtgg ttttgtctgt ccctccgaa cctgttggag    1740
cagttgttgg agctggatgt aggaacatga tgttaatgat gtatgtgttt tgtgtctttt   1800
ttagacactg gcactctagc tccctgaagt ttcagcagca ttgagtaagt agccagtgag   1860
tagccctcat tgatagatag gctcactaaa tgtgcagatg accaattcgc aggttagaga   1920
aggcttccca gaagaggagg cctctcagtg agcctagggt gttcagctca gcataatagt   1980
gagctgaagg ccccaatgca gcagcaagaa accacccagc aggacggcgg agttcacaga   2040
gaggggagag ttcatagaga gggagagtgc cacaggccct ggcacagctt caagccctgc   2100
tggatgttgg tgctgagcct cccctcctgg agcctcagag gggcttacag gggctctgga   2160
gatcccaact gtgttgcttc ttggcgtcat caccccttcaa tggagtctga gagctacccct  2220
gggagatcca agtgtgtgtg catgtgtgtg ttttttcttt ttggaaattt gatgtcccca   2280
gcatttggac ctgctttctc cacatatatg tagtgggagt gtgaccggag ccccactggg   2340
atttcttagc tagtgacata gcttcagtgt ccagaggcat catggcttga caaaagaggc   2400
actccttgga ggtagccaac tgtgcttcct ggcccatgaa tccacaggaa attggaactt   2460
tcagttgcca caaatcctgg gtcctagcct cacaggtggg tgtgttacct tcccggaagc   2520
cagtgagtac tatgaaagca gaggctgtcc ctgaggttgc aggcagaggc cacagagggg   2580
aacatgacac aggaatccct acaaattcta cttggggctg cctaaagaag agggaagtag   2640
```

```
tgaagcaaga agaagcacat ggcatctctt ggagttttac attgacccct gagggttccc    2700
cggcttactc tagtcacttg ttcctgcttt gctgcctcca tcccacattg ggctgagtga    2760
tggtggcatt gatgagctcc caaaggccag ctgtgccagg gggtctgacc ttatcttgct    2820
gccaatgtca gccttttgtt ttttaatatt tagactattt atttagctgt cttagcagtt    2880
tcaaaggagt tatgtgccct ttcacctact tatatgttgt cagtctttgc agggaggcca    2940
gattaatgct tagatctttg ttttgggcta ctggaatgct tgacttgaag ttcagagctg    3000
cttgttccca ggtgaacagc tactgctgga agttgctgca tcaacattct aatggctttt    3060
tctatggcct gttgtctttc aacccaaacc tggcctgctg aacactgcat ctagtcccat    3120
gcctgctaaa tgtctctaag cctgccctct gccccaaatc atacataaag gtgtttgtaa    3180
gtacactggt attgaattac tagtcatatt ttttccactg aagactggaa cctcaggtgt    3240
cctgtttgga tttttttaat ttgttcaagt taaagtacat acatgtagta ccaaactttg    3300
tggtggattt agatctttgc gtcttcctca atttctgaca caattctgga tgcagaggga    3360
ggttctcagg aaaatttta ttgaatgagt taatgaataa tttaagaaat catctctaaa    3420
gtttgagaac taaagaaaaa tagttcagtt cttagaaggg aaacttgagg gtggctgaaa    3480
aggattgact ggaatttttt aaaggaaatg tgactccccc tgcccactga ctgggctttg    3540
gatgccacat ggatgtggaa tgaggtgttg ggattggcag agggaatctg ctagcaatta    3600
ataaataaat aaatattggc agggcgtggt ggctcacgcc tgtaatccca gcactttggg    3660
aagccaaggc agcaggtcac ttgaggtcgg gagttcaaga ccagtctggc caacatggtg    3720
aaactccatc tctactaaaa atacaaaaat tagctgggtg tggtggcaca tgcctgtatt    3780
cccagctact gggagactga agcaggaga atcgcttgaa cccaggaggc gggctttgca    3840
gtgaaccgag atcgagcctc tgcactctag cctgggcgac aaagcgagac tccatctcaa    3900
aagaataata ataatattaa taaataaaaa tgatttatga ggtaaaagag ttttatgccc    3960
ccatgttcca ggaatagttt ggtggtccac atggttctcg gctggcctct cctctggccc    4020
ctcagtcatc cctggggtac tggggaatta gccaacccat catgcagtgc ttcttggcca    4080
tggactgccc catctgctgg aaacctgggt tgtttctgag gttgtctggg ctgtccgctc    4140
tttggtttca ccatagctct gtccagccta tggacagaca ggttccttga gaaacttccg    4200
gctgggtgtg gtggctcatg cctgtaaacc cagcactttg ggaggctgag gcaggtggat    4260
cacaaggcag gagttcgaga ccagcctggc caacatggtg aaacctcgtc tccgctaaaa    4320
atacaaaaat tagccctgcg tggtggcggg tgcctgtaat cccagctact cgggagggag    4380
gctgaggcag gagaatttct tgaacctggg aagtggggt tgcagtagcc aagatcgcac    4440
cattgcatgc cagcctgggt gacaagagca agactccgtc tcaaaaaaaa aaaagaaaa    4500 agaaaagaaa cttccaagct gctctgcatc gccttgctct ccacctgtct gcttctaaga    4560
agccctcggc ccagtcctgg gtgggactcc cactccctcc ccattgtcct ggactagctt    4620
ttctatcagc cttatcttgt gtagagacag atagtcttag aagatgagag agccctcact    4680
gttatcccca aagctgcctg gaggaaaagc cagagcaacc tgggagctgg gaccggggct    4740
gactctgggc agcagagacc cgagagacct ggaacttgaa cctcactgtt acgcctttgt    4800
tgatttctct cactcagggg acacacagac cctcatccag cctttgcag ctatatggca    4860 aggcagagaa gccacttgcg gggtcccgtg gcccactatg cacgtacata gtagacacat    4920
ctggccatga gtggtcagat tgagccactc tctagctagc tgacacctgt catcctgggt    4980
caaatttctg acagttgaca caaagcaggg ggtcagggag ccaaaaaaaa aaatggccag    5040
```

```
gtgtggtggc tcttgcctgt aatcccaggg ctttgggagg ccaaggtggg cagataacct   5100
gaggtcagag ttcaagacca gcctggtcaa catggcaaaa ccccgtctct actaaaaata   5160
caaaaattag ccaggctggt ggtgcatccc tgtagtccca gccactcagg aggctgaggc   5220
atgagaatca cttgaacccg ggaggtggag gttgcagtga gccgagattg tgccactgca   5280
ctccagcctg ggagacagag caagactctg tttcaaaaga aaaaaagag tattctggag    5340 attgaagttc aggagttcag ggttcatctc gactttgggc agccaagcaa gaactaaagt   5400
ataccaagat gttgaaggtt gatacctttt tatttatcga ttcattcact cacctatgta   5460
ccaaagagct cctgagcctc tcttcgatac aggggcact gccaggagtt gtagaggatg     5520
tgatagcaaa gataggaaat accttttctc tttgctctga caacggtggg gcaaggattc   5580
atcattgatt tcagcaggag gcaggataaa atgtgtgtag aatatagga atacatggca   5640 atcagtaaca tgtggtacct agcagcatgt ctgactgttg atacggtcag gctaggtaca   5700
tcccctcagg gaagaacttc tgtcttaggg gcacacaccc tatctttttt cccttcctgc   5760
caattcacag gtaagaacat ttagtcccag ggaactatgt catctctcta cttctcataa   5820
ctgaaaaagc agtgccaatt atgtatgagg tataggagac acaattctcc ctcttttaa    5880 aaatgtttaa tagctttatt aaggtgtaaa tgacataaaa actgcatgta gctaaagcat   5940
gcaatttggc acacatgtat ctctacaccc ttgaaaccat caccactaga aaggtgcatt   6000
tctccccagg aagaggggca agtctaggcc ctttgccaga gttgctccca gattgttttc   6060
aggttgggcc tgcattcaca gctcagccag ctgaagggtg acagcattag actcgtgacc   6120
caaatcttaa acccacacat tccattttaa cattgatacc tgtgatcatc agccagtata   6180
gcccatccca tgtgccaggc ggaggcatca ataagctggc tgtagcagc tttaatcaca    6240 gctggggagc caggagctaa ggaatgctag actcctttgt aaacaattta agtaggggt    6300 acttagcctg gactctatgt gcttctcatc cacctcttct cagggagatt ctggccaagt   6360
cctggaacct actgcagtcc atctggtggt tgacagatat gtggacggat tggcaggctg   6420
ggacccaatc tatgtttgcc cttgtgttca gttttgagac ctagcacctt tcctgatcct   6480
gctcacagac ccctgcggc caataggaaa gaagtgttaa tgcatatttg cttttggagg    6540
gcccaaagcc aggcccagag agttgtcaag ggcggtcagt ggtgggtgga tgcagagtt    6600 aaccaaggag ttacacacct gcctagacta aggacaggct ggaccaagta gagagggtgg   6660
ggctaaggga gcctgagaga tgctctgggg cctgtctcaa aatgagcact atagtcaccc   6720
tgtcccctgc agagattgtc tgacctggtt ttaggtcaca cccaaccttg ccagccaagg   6780
agtctttaga agcctgatat tgggagacct gtcctgggt ctacaacccc agaactcact    6840
gcagaagccc acgtggattg ctagtctagc tcagccatat gggtccccaa ccctcacctc   6900
atgatagtcc tgtgagaaac cgctgctgac cctttgttca tgttttcatc ttttccacta   6960
taaaagacat gctagctggg aaatagagcc catcatactc aagagtggca ggagccaggt   7020
cctggcccct gaagcttggc ctcacacaca gaggccggca ccctgtcatc aattccctca   7080 gcttttctc cgcctccact cccagtccta gatttagcag ccatgtgtgg gtggggcca    7140 ctgcagggat acttacccac ctaccagaga gatggcctgt gggtgctggc ccttctgagg   7200
ctgtggaggt tggaggctgt ggcagcctgg gcagtcaggc tgtggtcctc ccatgttctt   7260
gactcctgct agtctgggct gcctcctgat taggggttgg atgctccagt tcttccctgg   7320
gttggggatt gccacactac tcccagccca tccaggttca cgcttattcc aaagcggagc   7380
```

```
accagcagtg tgcctgctgc gggagttctc cgtgtccagc ctgagggttg cctgccaacc   7440
cctctgagag gtgcccggag gctgtgcgcc cacactgccc agcagtgcgg agaagcaggc   7500 ttgttttttcc ctgtcactgg cttggaagag atgctttgtt ctaggagcc gcatgtcccc   7560 ttgcctgcgt tgttggtgag gagccagcag gctccgtgga gggcaggcta gcagcctggc   7620
accagggagg caagggtctg agttcctagg agggtggttg ctcatgtgag aagtctgcaa   7680
aggttactac tgagcaccat ctctctgtct gaaaaacatt tttcattttt ctgtgaacca   7740 ctaagttttcc cgtttgggct ttcttcctgc ttttggctct tgtttaggca ggcgtagcca   7800
gatccaagcg tctggctgct tccccatgtc ttcagacctc tttttctgtt catggtaact   7860
atagatggaa ccacacattg gaagctggaa actcaagcgg tgcagcctat tccttacccc   7920
aatccctgtt ttacaaatgg ggaaatcaag gcacagcatg gggtgatgct tatctgaggt   7980
tggaagagtt aatagtagag tgggagctaa aacccagttt cttacctcca agctcagggc   8040
tttcagctgt aattgagcct agtatagttg gtgtgcagca tcagggattc cagctctaaa   8100
ggtcacaaaa aggacccggg ggtcattggc ccagggtggg aacctgagca gagcaggtcc   8160
agatggtgca ctctgtgccc tggccttagt ttccttgctgg atgctttggc ccgtagagcc   8220
ccagagccct gcttccagaa ccactccagt gacgttcatg ccaatggcct gaaccccact   8280
gagcgagggt gccctgcctc ttccacagcc ctgggctccg ctcagatttt taggagcaag   8340
cgttagaggc cttgctttct ccagggtcag catgtggaca gaacacttac tctctgcctg   8400
tctctcctcc tcaaaatgga agcaagacag tggggcctac aatgctatga aaaacaggat   8460
gggaaagaag cctgctctct gccttcctgc ccaggtgagc catcacctga ctaagtgagt   8520
tcacactcag agcgtgtggg gatggcagga tgttctgact tcattttcca ggatgccttt   8580
gctttaaaac cttttaaaaa gaagtgaatg atacaccccc tttgctcatc ttgcagtgga   8640
acctggtgtg tgaggacgac tggaaggccc cactcacaat ctccttgttc ttcgtgggtg   8700
tgctgttggg ctccttcatt tcagggcagc tgtcagacag gtaaggtgtc tgtcttctgg   8760
agcaccaggg gacctcagca ctgaggaaga agcgtgtgcc tggcccttga tttcagttgg   8820
tagtattctt tcagcgcagg gccctgtatt ttaaagaaga ggaagctatg tctgtgatat   8880
agactccatg cctagtaaga agagccaaca aatcatctga ctccgtaatt cttgctaagt   8940
aaagaaacct gagctgtcta agctgaatgt atctgtgatc cggttgacta ggtaatatgc   9000
catgattcac ttctgcagta gcctggcttg cctcccctgg gtcactgtga ctctgtcatg   9060
cccctgagca tgggagaggt tgacatcatg cacacatgca catgtgctag attgtagatc   9120
tgtagtagtg ccacggtgtc tgcctctgta gtcccaagaa gaccagcatt ctctctgcaa   9180
agtgaaagga gctctcacca gccactagtg gtatgaaaag cagaactctt ttgtccacaa   9240
ggctgatgcc cctagctaa gtggcctgtg gttttggcat ttactttatg acaggaggga   9300
gaatagtgtt ttgatccatt tcttataagc aggttatttg tataattcta aagcttttaa   9360
ctcaaggaaa cattaacggc ttagagaatc ccaaacccct cgaaattata tgcacaatgt   9420
tagagactac atgtgagcat tttttggag agaggtccgt agctttcatg aagttcttag   9480
aggggtccat tatgttgtgt cttctttccc tggagcttca gggtctgtca gagaagactg   9540
tgaagagagt agcagccttc agcaagtcct tggccacatg gcacatgtga gaacacccca   9600
caaatcggtg ggttagccgg tggaaaggag tcccagcatc ttccctggtt tttaattcct   9660
ggcctcaagc aatcctccct ccataacctc ccaaagtgct gggattacag gcgtgagaca   9720
ccatgcgcag ccagatattt tttattgttg ttgttttttt ttggaaaagg agtttcactc   9780
```

```
ttgttaccca ggctggagtg caatggcacg atctcggctc actgcaacct ctgcctccca   9840
ggttcaagag attctcctgt ctcagcctcc tgagttgctg ggattacagg catgcaccac   9900
catgcccagc taattttgta ttttaatag acacaaggtt tctccatgtt ggtcaggctg   9960
gtctcaaact cccgacctca ggtgatccac ccacctcggc ctcccaaagt gctgggatta  10020
caggcgcgag ccactgcacc tgcccagcca gattttttt taaaaagcag gttaacctgt  10080
ttattattcc tactttacag atggagaaag tgagacagag ggattaaata acttccccaa  10140
ggtttcacag ctggcaagtg gcagagttag gatttggacc caggtagtct tgctcctcta  10200
ttgtgtatgg actactgttc taggtccctg ctgtcctaaa acttgctttc tagcaaggtg  10260
gaatgtatta acaaccaag tgaggaagtc gttgttgtcc ttggccatgg taagagatac  10320
agagaagtgc agggtgccac aggagtgtct aacagaggag gtcagggca gcatccctga  10380
gaaggtgaag catgagcgag agtgggaaga tgagtcgaaa gtagccagct gaggggtaga  10440
gaggagaaag aacatccagg cagggagaat agcaagtgct aaagccgggg ctcatgaaaa  10500
ggcatgggag caggacaaag tccgtgtggt agaggtgcgg agagtggtgt taagatgaag  10560
gggagaggca ggcagagccc tgggcagatg agcaaccagg gcttagtgga tcacagttag  10620
gactttgggc ttcagccaca gagcagcggt gggctactga gatttttttaa agcaatagtg  10680
tgacaatcag atttgtcctt ttttttttt taaagatgct ttgacaacct tgtgaagaaa  10740
gaattgaagg gaagcaaaag gtgttgtaga gagaccaatt aaaaggttgt cacagtagtt  10800
catgccagag atgatggtgg catggcctag catgacggtg gtagaaatgg agggaagtgg  10860
taagaggtaa aatcaacaag acttgccgat gggctggatg tcggaattgg gggaagaaag  10920
cttttctggcc tgagtaactg ggtgaatgaa ggtacacttc tctaagacag agaatgctgg  10980
aaaagaaccca cgttcatgga tattgagttc aatttgtgtg tactaaattt ggggtgacta  11040
tgagacccct aagtgagaa gtagagtgtg aagctggctg tatggatatg gtactgcatg  11100
agaggttttg gctagagaaa cacatgtagg atttgtcagc atatagaacc ctcagcagag  11160
ccccagatag ggatgaggtt gcctggggag aggggagtgg ggaggggagg ggggaactgg  11220
gggaggattg tgctatgctt agaggccacc tgagtggaca tgggagattc cttctcacgg  11280
agctaagtga cagctgcggc tcagaagaat gcccttgatg tgaaaaggag ataccccaag  11340
ttcagagtag aaatgcagtg tatttttctg ggtcagctgt gtcatgggtc agcttaagaa  11400
ccttcttgcc atgtgacaca atgattacct gaggaaagca tttaagttcc aaaaggtcta  11460
ttcccaggga aagtggaaac aaaatttgtg agtgtgttta ggaccacttt agtctacaga  11520
agggctaata tagtgttttt caaaccttc taaacatttt ggccacagaa ctttcattaa  11580
agtaggataa tttaagtcta gtaaatgaaa tacacccctaa gtggctaaaa gtatggctgt  11640
tctgcctgca gcccctgcct tcaattccca atgccctgcc tcaagcctgt ctgtgcccccc  11700
ttggaaggcc cagggccctg tgggatggac agcttctgag tgcattactt ctgagtaaac  11760
cagttctaaa acctaagcta agtagattac ctgaaagcaa tcaattcatg ccctaacttg  11820
tctaggacat caatgtaact ttttatatag tataaaggtt tcaccttctt tctggcctat  11880
gaatatgtct gaaattcaag agcaattaaa gtactcctgg gttgtcaaag ccctttatgt  11940
aacactattg agttatcttt atgcgtctga cttgtaagag atgcacaact ctaggaagaa  12000
gtagactgct gtgtcctgtt tccaggtatg tgtgtgtttg ccattttgtt gacagacttt  12060
aaaagcaaac atttctggcc ccaaccctga actgccaagg actggtgcta tgtaaagggt  12120
```

```
tctctggatc tgtctcttcc ctaccatccc agggagctct taggaaggga aagggcatag    12180
agattatacc agcctgcctt gtggttagga accacccctg ggttggcata tagaacatgc    12240
ttgttaaaaa aaccatgcag gggaaagtag agtctactac caggcgagag tttctcaacc    12300
tcgaccctat taacattttg agccaaataa ttttgttcta gggcattttc ctgggcattt    12360
tagaatattt aacaacatat ctggcctcta ctcattagat gccagtgaac cccaagtgat    12420
ggaaaaaaaa aacaacaaca gaaaaaaacc tcttttattg aggaaaaaca ccaaactctt    12480
ccacatagtt gcaagacctt gtgcaatttg cctcctagcc accactgtac tcttgaattg    12540
cacgcctgat gccaaccaca ctggttcctc atgttcacca tgcccctcc agccatgggg     12600 gtgtgtggtc ttctcagagt ctgaagcatt ccccacccac cccaacccac cccctgtggc    12660
cttctttaac catgctggct aattcaggat ccctagttcc ttatgacttt cctttaaaac    12720
gtctaccaga aattggggga aaaaagtgt tattatagga ttaatgttgg tcttccccac     12780
tatactgtga atatcattga gagcttggtc cctacacctt aaatcccccca tcgtcaacta   12840 ttttttccca tctcagtgtc ccatgatcaa ggagaccctc cctgaatgtc cagttcccca    12900
acccttaccc ccagtccagg gtagcttcct tccttgtgcc tctcattaac ctgcatgccg    12960
atccttcagt gcacttgact cagtgtgtaa ttgtatattc agtagcgtgt tgttagatta    13020
aaatgtggtt aatatgtgtt tcaccagtta tactatgaca ctccttaagg gcagaaacag    13080
catctttttt aatttattga tatccaagtg ccctctataa tagatgctca ataaacattg    13140
aatgaaagtg ggtgtcagcc agtactggcc agactcaaac tgaacccact gcttcccact    13200
agcttgactt tttcctcctg tttgtggcac tctctttaaa acaaaccaaa ataaacccaa    13260
ttttaaaaac tttttaaaat gagcacggat acagaaaacc acacagaaca aatgtgtagc    13320
ttaatgaatt tttttcagag aaataaacctt atgaccacca ccaagtcgag cagtagaact   13380
ttgctgtcca ctaagaagcc ctgtccatgt gccccatccc aattacagca tcctctctct    13440
ctccccatta agtaaccgct agcctgactc ctgtaataat cacttccttg tgagtttttt    13500
tagtttattt atcgaaatat gcatccttga cacaaattta gtgttgccca cttaatatat    13560
ttgatgtctt ttagtctact taatctatgg attctccttc tatcgccttc tatgccttac    13620
tgattatcta tgaagaacct gagctattcc acctatagaa tttcccagtc tggatttgtt    13680
gattgcacac tgatgatgca gttcagcaca ttcctctatg ctctgcattt cctcaaaatt    13740
ggcagttgga tccagagact tgagattcag gttctgattc aggttcagtc cttttggcaa    13800
gaccatagga agcatgcaat tcctgactgt ctctttatga tgttaacagt aattagtata    13860
taatgcatag atctattaat ccattggggg ctataaatgg tattattcta attttattac    13920
cttttcattt aaaagttaga atactttgt acatgatact acctcttatc tattattggt    13980
tgctgttcac atagtttaca aaggaaaatc aggacaaatg cttctttctc tttatttgcc    14040
agttttcatt tataatgaat tgtttctctg ttattctcca aatttggcag attctttttt   14100
aaaaaaaata tcattatgaa tgtatggatt aaataattga tgtatttcag tctcttgcaa    14160
tcattatcat aattgtagca ttgctttta ggcaaccctg gtacccaggc tgtacatttg     14220
tcatggggag tggggagggg gagaaatagc atgggcactg tgagaccgag actgtccctg    14280
gcagccagta ttctggcaac actgttcaca cccacttact ggatggatct tgagaaagcc    14340
ccacttggtg gagcccattc ctgctgccct tttccagctg gttatctgtc actctccttt    14400
tcttcccagg tttggccgga agaatgtgct gttcgtgacc atgggcatgc agacaggctt    14460
cagcttcctg cagatcttct cgaagaattt tgagatgttt gtcgtgctgt tgtccttgt     14520
```

```
aggcatgggc cagatctcca actatgtggc agcatttgtc ctgggtatgg ccatcaggtt    14580
ggagttgagt acttgatcct gtatttcacc atcatcccat cacctacctt tctggagaca    14640
gctgtgatgt ccctcaaggg ggacagggtt tctaacaaaa ctagccagag cttcctggtg    14700
aaccttactt acaggcaggg aaactgagcc agacatgaga ccagcctggg gtccccagca    14760
gcacaatggc ctgacttctg atttccagtt cttttctggc ctctgggctg tggctccttg    14820
gtcttagtac ttggtagtca atttactagg actcaccaga gatcctccat ttacaaaaag    14880
ggcctgccac tgcacagggc tgagccagcc cagaaagag ggcggcatgg ttggaggagg     14940
aggggctgtg actggcaagc ttgctaaggt agagaacccc ttgtctgcag agcactgtgg    15000
ctggtgatat ctacggacaa gaataaattg ataggaaggg gctttcgtca ccttcagggt    15060
tttaattcag agtgcacact gcagggcttt gtctcaaatg tgccagcctg ttgtcactga    15120
gaagctgcca ggccggcctg tgtttggagg aacctgactc tagctgataa ggcctttgag    15180
ttccttgggt tgtattgttg aaagggttgt ttttctttt tatatttaat attctttcct     15240
tgaggcttaa gtcagcatgt gctgacttag taatgacttc acttttaata aattcttcct    15300
catgtgagga ttaaagggg cctaccatgg catctttagc acatggcttc agaacatggc     15360
gaaattttca agagagaact gttgcttggg ggcctgagag ccacaggga tgtaccccca     15420 ggagacagtc agacaggagg ggttcagaac gccatccgct ccctagcgcc atgaacttag    15480
agagagttct cgctgttttc ttgtctgtgt attcacaaag ataccataaa aaattaataa    15540
ggaaggaacc caaattaaac tgctaactcg acctcccttg ttttgaacag ggacagaaat    15600
tcttggcaag tcagttcgta taatattctc tacgttagga gtgtgcatat tttatgcatt    15660
tggctacatg gtgctgccac tgtttgctta cttcatccga gactggcgga tgctgctggt    15720
ggcgctgacg atgccggggg tgctgtgcgt ggcactctgg tggtgagtgt gaccctgtgc    15780
cccatgtgcc cactggcagg atgatttctg tctggcnttc actagagggc agcaacaacc    15840
catgaatccc tattttgtct cccagagaca ggaagcatag attataaatt atttcagaat    15900
gttttctcca cactcaaaag agccaaaaca aaacagaatc ccatgacagc aacagacttg    15960
ctctcagccc tgtgctgggt tgccccaagt gtggggaaaa atagcagtag ctgtgagaag    16020
atggggtcca gcatgcccctg taggaagttc ccaagcctca gggcaggaca gtgtaggccc    16080
tagttctggc tgtgtgctgc tgaagcctca tgccacaggc actggcacca aaagcaagag    16140
tcctcagggt agccacatgg aggaagccag gctccttctg caccaccaag gtagaggagt    16200
tgaacaggca gagaagaggc cattccagac caagagggga acactgcaga ggtgctaagg    16260
tgggaatcac cccttgcagg tggagaaggt gagatcacca gcccaagtgg agcagagagc    16320
atttcagggc atagtgggag agtaagccgc acatcatggg gcccagtcat gaccgagggt    16380 gggggggcggc tacctggtcc cagcaaggtg gaaaataata tccatagagc actcaagtgc    16440
cttgataaac atgctaattt ttttcctttt tttcttttct tttcttttt tttcttttt      16500 tttttctcag acaaagtctc tgttgcccag gctgtagtgc agtggcgtga tttccactta    16560
ctgcaacctc cgcctcccca gttcaagcga ttctcatgtc tcagcctccc gagtagctgg    16620
gactacaggt gcctgccacc gcacttggct aattttttt gtatttcttt ggagagacgg     16680
gtttcactgc gttggccagg ctggtctgga actcctagcc tcaaatgatc caccggcctt    16740
ggcctcctaa agtgctggga ttataggagt gaaccactgc acctggccaa acatgctatt    16800
ttaggtagag tatctgacta atctgttgga taaatcaggg gtagggtgag gagagaagag    16860
```

```
aagctaaaag gccagtgcag aagcttctgt tggtgccggg gacagggagg agagtgtagc   16920
agggcctggg ctgacataga catgcacaga agccaggctt ccggagccca tcttgcaccc   16980
atctcctcag cccagcagat ggcaacactg ctcttcagaa atggaggtgg ccagccagca   17040
tggggatgcc gtcagggggt gcagggctct cccattttg tgcggtgtgg ggtacacata    17100
agctcatcca ccccaggtta ttgctgcgtg tggatcagct ctttgcttct ggcttgtgat   17160
caccaaacat tccacaagct ctggttctgc aaccttattc ccacctatgg ctgtgctcta   17220
cctggtctgt gggtctgctg ttggcaggga ggcctcactg agattggacc ttgtactgcc   17280
aggttcatcc ctgagtcccc ccgatggctc atctctcagg gacgatttga agaggcagag   17340
gtgatcatcc gcaaggctgc caaagccaat gggattgttg tgccttccac tatctttgac   17400
ccgagtgagg taagcaccat gtgggtgtgg gtgagaggga cagactgacc gtgatttgag   17460
agcagcagca cccagccctg aagtcctccc tgctcacagc agcccagccc tctctctgcc   17520
caagccccaa ctgcccattc cccccatccc cccactcccc accccacac gggccctgtt    17580 aacactcaga agttgaggaa taggttacag ctgcctcact cttttcacca cgggtttcag   17640
attttcattt tttacttcct ttctaggcaa tcatatattt taaccattac ttctaacaat   17700
aaatactctt tttgagtaat aggcctttca taaagtcagc atttgggaaa atcattgttt   17760
cttataccta aggtggcttg tcaccttaca aagctaaccc caaacgtaaa atgtaaagca   17820
caaatagatt tggagttaga agtatttcat ctcttgagta ttagcaatta ttcattaaaa   17880
agaaaaaaaa agtgtttagt ctctttctgc cctccaatgg ttaattattg catatcatct   17940
tggagtcagg tcctttttga tgtccacctc ttcccctac cccaccctc ccgtcagccc     18000 tgttctcaca caccatgact catttcttgg ctctacctag ttcctggttc ttgcttttcc   18060
ttcccgttcc ctctcctacc atctctgtag caggcagttt tccttggtct cgtgactatg   18120
agaggttaga agctgtaaat gctgcctggt gggttctgg aatgtgtctg tggtctgact    18180
ggaagatgag gggttgggtg tgggaacagc cacaagcagc cctgctgaag tgtgagaggc   18240
aggcatggtt gggcttggaa agagggaac agttattgta gacagcggag gccaatggcc    18300
actgccagcc ctgcagactt cccagtgagt ggtggcccag cagccactgt cagcatgcac   18360
cagaaagggg tcctgtgcgc aaaggtcagg caggagtgtg gcagagggct tttaagttag   18420
gtggttttgg gggcttttaa gtgaggggtc aatctgggtg aatgcataag ccccactggc   18480
atctttgagg aaatgaggct atttcagggg atactttcag tccaaagttg accttttgtt   18540
gaacttctaa ctctggaaaa acaagctcca aacctgggtt tgcttaagaa agcaacatca   18600
gtgtgtttag acgtgtggtt tattaatggc cttggctgtg ctgaatttca taggaagtca   18660
ctctgggtga agctcaggtc aattttcctg tttttctatt tgaattcttt ttccctggaa   18720
gcacaccagt aactacatag tataaggact caaaacatta acttttaaaa aatatcagac   18780
caataaacca cacagccagg tactctctct gacccagagg gcagggagcc aggcttcggg   18840
aggaatactt agaggcctcc ttggaatgtg gccaccgaca ggaatatgtg ggggtgcagt   18900
gaggaagctg tcagcctggg cctctgtctt cctgtaccct tgagggactg gtcacttact   18960
tttcctcatt ttcattcact ctgatttgtt actgacaagg cctaggaag ttttcacagc    19020 ctaaaacaca gtcagtatac ttactgttct tagaaacgta acactcccg acgctgagat    19080 gcagacagct aagatgccag ggattcaagt atgttattgt gtgctctgag tctctgacca   19140
cctcttcttc ccatacactt atgatgttgt tcctgcagtt acaagaccta agttccaaga   19200
agcagcagtc ccacaacatt ctggatctgc ttcgaacctg gaatatccgg atggtcacca   19260
```

```
tcatgtccat aatgctgtgg tatgtaaaag agacctgcct gaggcttcca gacaaagctt   19320
cttgaagtgg ccattgggcc tcttgtttac agacatgcct cagacaaaat tcaaagccta   19380
tgtcatcaga gagtgaaaag gatatgtctt gtgttagatg gaaaaaatgg gcatgtcaca   19440
attcttaatg ggatggaacc tcagaaaagg agaatgaaaa caattgtgga ggctgttgtg   19500
ggaaatatgg actctcgtgg ggaatctctc cagatcttaa gatgaatcct tgcccaattt   19560
gggtcattta gttcccgtct cctacccagt taccgacagt ggctgaggag gccaggtagg   19620
gcttttaaga aggatctgag tgaagacacc atgtcctgta ggctgcagag gctgccagtt   19680
actttctgga aatgtggaag tgggatgtgc tcctcctggg atgtccataa acggtcctgg   19740
agtcagggct atagcctaga tgtccttacc aggttcccac taatgaggca aagtatgtca   19800
gaaagggatt tgtgaattac cagggagagg aaacatgtcc aagtgcacat cgctagcttt   19860
tgctcagcgg ccgaaccctg ggattctagg cgacttctgg agcctggtgg gttagcggtg   19920
agaagatggg cgaggagggc ggacttcatc tcagagtcct tattactagt ctcatccagc   19980
tttgaggcag tcagccactg tgcctactga gggagtgcta tgagtcaccc gcttccaagg   20040 aatgcccag gatccctcca ggcagttcac cattccctga gttggcctca agacaggagc   20100
agcatgtagc ctgcaccaca gacatgcaag cctgtgatga gtcacccact tttgtgttca   20160
cccaggctct cctccctgct ctggatttcc tggggactga tgcacatact cttttattg   20220 taccagctgt gtgttccacc tgcagatgag tcaaaacagt ctaatccata aaggtctggt   20280
ttgtcaaaga gtgtgggtca tcaacagaga gaatgcctac tggggatgcc caggtcaggg   20340
gtactgcagg gcatcctgat gagaggcagt gtggcccctc cattgggagc cacctctctg   20400
ctccacaagt accgcggggc tggtgtcagc tgtctctgac cagcctcttc ctgactggtc   20460
accacaggta gtgtgtgagg gtctctctcc aagtgtttga cctaatgttg ttccttttgt   20520
tatcttatcc cccaaatcct atcacacctc acttgatgtc tgcctcctga ctcattctct   20580
agctccttct gcagttgctg gatttgagga ggttcagctt aggatttta aagctgaaag   20640 gcaggttgga attttctttt tcaatgaagt aaatctatct gaattataca gcttttttg   20700 ctgggacact gtctatatgg aaggctctga gagcgcactg gcgcagggtt tacactgtac   20760
cacttgggct ggggaaaatt atcttttgat ctatgaagta agacgcaggg ttacagttac   20820
tgctgcctta ctagtctctg cttaaagatg gtttggaatt tactgaaata attgcattgt   20880
aaaagttgta caggttggga aagatgtgga tactgctttt ccagctttct tctgcactct   20940
gtttcaggat gaccatatca gtgggctatt ttgggctttc gcttgatact cctaacttgc   21000
atggggacat ctttgtgaac tgcttccttt cagcgatggt tgaagtccca gcatatgtgt   21060
tggcctggct gctgctgcaa tatttgcccc ggcgctattc catggccact gccctcttcc   21120
tgggtggcag tgtccttctc ttcatgcagc tggtaccccc aggtagggac catgtgcatc   21180
tatggtttgg ggtcttcact gagtctctta ctgtctacca ggctgtctca attaataaag   21240
agaataaaat caagcccatc acagctccct tgcttatata cattcttggc ctaaaaatca   21300
atagaaagtg tcttctgaga ctagaacact tatggcctgg gctttgaggg agtgggaaaa   21360
agcagccatt ggggctgttg gttaatttta ctctgtaccc aagttaatgt gctcatactg   21420
ttttccactg cagaagaaga gggaagaaat agctatccca ttccttttt tcctggccct   21480 gtcttcttta tttattcaac aaatagctat ggcatgccta ccatgggctg gcactgtgc   21540 tcggtgataa cgatacacaa gaaaacaagc caggcagaac cccaggccct catggaacgt   21600
```

-continued

```
acaccctaga tgagaagaca gacaacaaac aagtaaataa aatgcttaat atagttcaga    21660
ctgtgttacc ttctaggaat acaaatgaag gacaatgccg agttagttta catagtcaca    21720
gatagtgtcc ctgaacaggg ggcagttcag tagaaatgta cataaagtga cagaaagccc    21780
tgaaaaagtc taggagaaca ttttaggaag aagaaatggc aaaggcagcg accctgagca    21840
ggggatgagc ctggcatgtt tgaggaggag ggagaagggg aggggccaga ccactgagag    21900
ggcctcacag acccttagca ggattttatt tctgaaacta tcttagtatc ccacagatgg    21960
gtgggaggta gccatttcca ataatttata gaacagttca tgggccctca tctctccctc    22020
tccatcactg tgcccagaga cttcagtgta cctgtagatt tgggagcctc tgatggtcac    22080
ttttgggccc atcaggctga gaacactgca cgggaacagc tccccatggg atgtggcagg    22140
aggagcccag aactgatgta gaggctcaca gctgagctca gagtgacctt caggtcacac    22200
atagctctcc catcagcaca gcacagagag attagaagat caactcgaga ttctgatggc    22260
ctatgatttt tttgaggtct gagtgggagg aaagcatgaa atgagttaga actgaattct    22320
ccattcatct aaacatcatg agttaattcc atagtgcctg cagtgtgagg ttctggggtg    22380
acagttaatc cctgacagac atgtctttaa tgacttatag actgggaagc aggttgattg    22440
gactattaag gagcttactc tggtggtctc caggttgagg aaagtgcatg tccttatagc    22500
tgcaggtccc agcctccttt cagcaatcaa ttttggaggga aatcttggct atagcccctt    22560
cccccacaat aggaagtgat agaaactgac tccccaaaaa atttgggaag aaagtatgtt    22620
tgttttgctc tcaatagctg catgccatgg gttggtacct actcctaccc tctttccttt    22680
gcttctccag acttgtatta tttggctaca gtcctggtga tggtgggcaa gtttggagtc    22740
acggctgcct tttccatggt ctacgtgtac acagccgagc tgtatcccac agtggtgaga    22800
aacatgggtg tgggagtcag ctccacagca tcccgcctgg gcagcatcct gtctccctac    22860
ttcgtttacc ttggtaagtc ccatgagcca agggcacact agagcaacgg gatggaagta    22920
ctaactggct tgaatgtgag ctggaggttg cgtgttaaca ggaaaacaag ttcatacagt    22980
acatgggctc catccagtac tggatctttg gccgggaagg gttcttgtcc cagtgcactg    23040
gccctcactt tcaaatggaa aacaacctat agattaccta gaaattgatg agaatattag    23100
agggtttgtt tctgttttag ccatcccagg ccttccatca gagactacaa ttcctttatc    23160
ctaagaacct acagagtggt ttagggagcc agtgtgctta gttggagaaa tttcttggaa    23220
tcagagttta aaaggaacat gaggggaaag atgtccatgc aagaggtctg atgaacgtaa    23280
aattattata acctagagca ctatagagtg attttatctt gtgtgaagat ccaccccatg    23340
ccattttatg tagcaggtct ccagttttct cttctcagaa ttatgtcttc atagcacctg    23400
tggtttccct gcacatccct agccagtacc tctttaggga gggtggcacc cacctgagag    23460
tactcagagt gctttgtgaa catgctatgt agatctcaaa gcaagcaaaa gcaccctgcc    23520
taatctgaag gcagatcaca tgggctggga cacatctgca gaggtggaag agttatttcc    23580
atccctggac aagtacctca ggttccttgg aaacccaacc ttggtaaata agaataatca    23640
gcatggccca gaaataggaa taatcagcat ggcccagctc ttctcctgca accgcccctt    23700
tgtactcctc ccctgcatgg tggaacactg ctgggctctg ggcatgcctg tgccagctct    23760
gggttctgaa acctgtctag atgccagatt ctaatctgac tgctcagact gtgagagatg    23820
tgagaccaag aaggaaagtg atccccttcc agagtcctgg gagcataaag gggtagatga    23880
gagaccaagt ctaactgcag ccctgggcct gaggctccgt ctgctttgcc ataggtgcct    23940
acgaccgctt cctgccctac attctcatgg gaagtctgac catcctgaca gccatcctca    24000
```

-continued

```
ccttgtttct cccagagagc ttcggtaccc cactcccaga caccattgac cagatgctaa    24060
gagtcaaagg gtaagaagac ctcctctgtc agtgttgatg cactgggtct gggtctggcc    24120
aggtctcagg agcccctcac aatagagcta ctcgcaaact ccctctcaca gacaccatgg    24180
actagtttag ccattaaagg gttgtaaatg gcaaggtgct tacttatagc ccatcctctc    24240
tggtctgttc ctgtgtggac atgtcactat acacatctcc atggcagtag ccgcactgga    24300
taactcagag gctagaagaa acctttcaga atctgctgca ggattctctt cccagggaag    24360
atatcctcag ttcttgtttg tttggagact gggaggcatc tttttaaaat gtgttactga    24420 catattttg cttgttttta tagaatgaaa cacagaaaaa ctccaagtca cacaaggatg     24480
ttaaaagatg gtcaagaaag gcccacaatc cttaaaagca cagccttcta acatcgcttc    24540
cagtaaggga gaaactgaag aggaaagact gtcttgccag aaatggccag cttgtgcaga    24600
ctccgagtcc ttcagtgaca aaggcctttg ctgtttgtcc tcttgacctg tgtctgactt    24660
gctcctggat gggcacccac actcagaggc tacatatggc cctagagcac caccttcctc    24720
tagggacact ggggctacct acagacaact tcatctaagt cctaactatt acaatgatgg    24780
actcagcacc tccaaagcag ttaatttttc actagaacca gtgagatctg gaggaatgtg    24840
agaagcatat gctaaatgta cattttaatt ttagactact tgaaaaggcc cctaataagg    24900
ctagaggtct aagtccccca ccccttccc cactcccctc tagtggtgaa ctttagagga     24960
aaaggaagta attgcacaag gagtttgatt cttaccttt ctcagttaca gaggacatta     25020
actggatcat tgcttcccca gggcaggaga gcgcagagct agggaaagtg aaaggtaatg    25080
aagatggagc agaatgagca gatgcagatc accagcaaag tgcactgatg tgtgagctct    25140
taagaccact cagcatgacg actgagtaga cttgtttaca tctgatcaaa gcactgggct    25200
tgtccaggct cataataaat gctccattga atctactatt cttgttttcc actgctgtgg    25260
aaacctcctt gctactatag cgtcttatgt atggtttaaa ggaaatttat caggtgagag    25320
agatgagcaa cgttgtcttt tctctcaaag ctgtaatgtg ggttttgttt tactgtttat    25380
ttgtttgttg ttgtatcctt ttctccttgt tatttgccct tcagaatgca cttgggaaag    25440
gctggttcct tagcctcctg gtttgtgtct tttttttttt tttttaaac acagaatcac     25500 tctggcaatt gtctgcagct gccactggtg caaggcctta ccagccctag cctctagcac    25560
ttctctaagt gccaaaaaca gtgtcattgt gtgtgttcct ttcttgatac ttagtcatgg    25620
gaggatatta caaaaaagaa atttaaattg tgttcatagt ctttcagagt agctcacttt    25680
agtcctgtaa ctttattggg tgatattttg tgttcagtgt aattgtcttc tctttgctga    25740
ttatgttacc atggtactcc taaagcatat gcctcacctg gttaaaaaag aacaaacatg    25800
tttttgtgaa agctactgaa gtgccttggg aaatgagaaa gttttaataa gtaaaatgat    25860
tttttaaata t                                                         25871
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
gcaggaccaa ggcggcggtg tcag                                           24

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
agactagagg aaaaacggga tagc                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8 agattttag gagcaagcgt taga                                               24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
gaggcagaca ccgtggcact acta                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
ttcacaccca cttactggat ggat                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
attctgtttt gttttggctc tttt                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
agcagggcct gggctgacat agac                                              24

<210> SEQ ID NO 13
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
aaaggacctg actccaagat gata                                             24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
tctgaccacc tcttcttccc atac                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
gcctcctcag ccactgtcgg taac                                             24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
atgttgttcc ttttgttatc ttat                                             24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
cttgttttct tgtgtatcgt tatc                                             24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
tatgtttgtt ttgctctcaa tagc                                             24

<210> SEQ ID NO 19
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 19
tctgtgagag ggagtttgcg agta                                              24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
tacgaccgct tcctgcccta catt                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
tcattctgct ccatcttcat tacc                                              24

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
gataagctta cggtgtcccc ttattcccat acg                                    33

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 23
cccatgccaa caaggacaaa aagc                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 24
tgtttttcgt gggtgtgctg atgg                                              24

<210> SEQ ID NO 25
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized Primer Sequence

<400> SEQUENCE: 25
acagaacaga aaagccctca gtca                                          24

<210> SEQ ID NO 26
<211> LENGTH: 10
<212> TYPE: PRT
<213> ORGANISM: Homo sapiens

<400> SEQUENCE: 26

Glu Gln Lys Leu Ile Ser Glu Glu Asp Leu
 1               5                  10

<210> SEQ ID NO 27
<211> LENGTH: 17
<212> TYPE: DNA
<213> ORGANISM: Homo sapiens

<400> SEQUENCE: 27
tcctgtggct gaccata                                                  17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 28
tcctgtggcg gaccata                                                  17

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 29
agggcggcat gcgggactac g                                             21

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 30
cttgcagtgg aacctggtg                                                19

<210> SEQ ID NO 31
<211> LENGTH: 19
<212> TYPE: DNA
<213> ORGANISM: Artificial Sequence
<220> FEATURE:
```

-continued

<223> OTHER INFORMATION: Description of Artificial Sequence:Artificially
    Synthesized Sequence

<400> SEQUENCE: 31
tttgccataa gtgcctacg                                                    19